US008063028B2

(12) United States Patent
Billedeau et al.

(10) Patent No.: US 8,063,028 B2
(45) Date of Patent: Nov. 22, 2011

(54) HETEROCYCLIC ANTIVIRAL COMPOUNDS

(75) Inventors: Roland Joseph Billedeau, Santa Clara, CA (US); Zachary Kevin Sweeney, Redwood City, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 443 days.

(21) Appl. No.: 12/341,594

(22) Filed: Dec. 22, 2008

(65) Prior Publication Data
US 2009/0170856 A1  Jul. 2, 2009

Related U.S. Application Data

(60) Provisional application No. 61/016,142, filed on Dec. 21, 2007.

(51) Int. Cl.
*C07D 487/04* (2006.01)
*A61K 31/4965* (2006.01)
*A61K 31/675* (2006.01)
*C07F 9/09* (2006.01)
*A61P 31/18* (2006.01)

(52) U.S. Cl. ........... 514/81; 514/248; 544/232; 544/236

(58) Field of Classification Search .................. 544/236, 544/232; 514/81
See application file for complete search history.

(56) References Cited

U.S. PATENT DOCUMENTS

| | | | |
|---|---|---|---|
| 7,166,738 B2 | 1/2007 | Dunn et al. | |
| 7,189,718 B2 | 3/2007 | Dunn et al. | |
| 7,208,509 B2 | 4/2007 | Dunn et al. | |
| 7,241,794 B2 | 7/2007 | Dunn et al. | |
| 2005/0215554 A1 | 9/2005 | Dunn et al. | |
| 2005/0239880 A1 | 10/2005 | Dunn et al. | |
| 2006/0025462 A1 | 2/2006 | Dunn et al. | |
| 2006/0069261 A1 | 3/2006 | Bonneau et al. | |
| 2006/0223874 A1 | 10/2006 | Martin et al. | |
| 2007/0021442 A1 | 1/2007 | Saggar et al. | |
| 2007/0078128 A1 | 4/2007 | Saito et al. | |
| 2007/0088015 A1 | 4/2007 | Silva et al. | |
| 2007/0088053 A1 | 4/2007 | Mirzadegan et al. | |
| 2011/0059975 A1* | 3/2011 | Kennedy-Smith et al. | ... 514/248 |
| 2011/0105496 A1* | 5/2011 | Gamber et al. | ............ 514/233.8 |

FOREIGN PATENT DOCUMENTS

| | | |
|---|---|---|
| WO | WO-02/04424 A1 | 1/2002 |
| WO | WO-02/30907 A1 | 4/2002 |
| WO | WO-02/085860 A1 | 10/2002 |
| WO | WO-02/100853 A1 | 12/2002 |
| WO | WO-2004/002951 A2 | 1/2004 |
| WO | WO-2004/002951 A3 | 1/2004 |
| WO | WO-2004/029042 A1 | 4/2004 |
| WO | WO-2004/031156 A1 | 4/2004 |
| WO | WO-2004/031178 A1 | 4/2004 |
| WO | WO-2006/067587 A2 | 6/2006 |
| WO | WO-2006/067589 A3 | 6/2006 |

OTHER PUBLICATIONS

Chan, J. H., et. al. "Novel Bensophenones as Non-Nucleoside Reverse Transcriptase Inhibitors of HIV-1," *Journal of Medicinal Chemistry*, 2004, vol. 47, pp. 1175-1182.

Genin, M. J., et. al. "Novel 1,5-Diphenylpyrazole Nonnucleoside HIV-1 Reverse Transcriptase Inhibitors with Enhanced Activity versus the Delavirdine-Resistant P236L Mutant: Lead Identification and SAR of 3- and 4-Substituted Derivatives," *Journal of Medicinal Chemistry*, 2000, vol. 43, pp. 1034-1040.

Romines, K. R., et. al. "Structure—Activity Relationship Studies of Novel Benzophenones Leading to the Discovery of a Potent, Next Generation HIV Nonnucleoside Reverse Transcriptase Inhibitors," *Journal of Medicinal Chemistry*, 2006, vol. 49, pp. 727-739.

Wyatt, P. G., et. al. "Benzophenone Derivatives: A Novel Series of Potent and Selective Inhibitors of Human Immunodeficiency Virus Type 1 Reverse Transcriptase," *Journal of Medicinal Chemistry*, 1995, vol. 38, pp. 1657-1665.

* cited by examiner

*Primary Examiner* — James O Wilson
*Assistant Examiner* — Cecilia M Jaisle
(74) *Attorney, Agent, or Firm* — Brian L. Buckwalter

(57) ABSTRACT

Compounds of formula I, wherein $R^1$, $R^2$, $R^3$, $X^1$, $X^2$ and Ar, are as defined herein or pharmaceutically acceptable salts thereof, inhibit HIV-1 reverse transcriptase and afford a method for prevention and treatment of HIV-1 infections and the treatment of AIDS and/or ARC. The present invention also relates to compositions containing compounds of formula I useful for the prevention and treatment of HIV-1 infections and the treatment of AIDS and/or ARC.

6 Claims, 3 Drawing Sheets

HETEROCYCLIC ANTIVIRAL COMPOUNDS

CROSS REFERENCE TO PRIOR APPLICATIONS

This application claims the benefit of priority to U.S. Ser. No. 61/016,142 filed Dec. 21, 2007 which is hereby incorporated in its entirety by reference.

FIELD OF THE INVENTION

The invention relates to the field of antiviral therapy and, in particular, to non-nucleoside reverse transcriptase inhibitors for treating Human Immunodeficiency Virus (HIV-1) mediated diseases including AIDS and ARC (AIDS Related Complex). The invention provides novel 1H-pyrazolo[3,4-c]pyridazinyl, 1H-pyrazolo[3,4-b]pyridinyl, 1H-pyrazolo[3,4-c]pyridinyl and indazolyl compounds, pharmaceutical compositions comprising these compounds, methods for treatment or prophylaxis of HIV-1 mediated diseases employing said compounds in monotherapy or in combination therapy. The compounds of the present invention provide high blood levels of HIV-1 reverse transcriptase (HIVRT) inhibitors when administered orally.

BACKGROUND OF THE INVENTION

The invention relates to the field of antiviral therapy and, in particular, to non-nucleoside compounds that inhibit HIV reverse transcriptase and are useful for treating HIV-1 mediated diseases. The invention provides novel heterocyclic compounds according to formula I for treatment or prophylaxis of HIV-1 mediated diseases, AIDS or ARC, employing said compounds in monotherapy or in combination therapy.

The human immunodeficiency virus HIV is the causative agent of acquired immunodeficiency syndrome (AIDS), a disease characterized by the destruction of the immune system, particularly of the CD4$^+$ T-cell, with attendant susceptibility to opportunistic infections. HIV infection is also associated with a precursor ARC syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Two enzymes that have been extensively studied for HIV-1 chemotherapy are HIV protease and HIV reverse transcriptase. (J. S. G. Montaner et al., *Antiretroviral therapy: 'the state of the art'*, Biomed & Pharmacother. 1999 53:63-72; R. W. Shafer and D. A. Vuitton, *Highly active retroviral therapy (HAART) for the treatment of infection with human immunodeficiency virus type*, Biomed. & Pharmacother. 1999 53:73-86; E. De Clercq, *New Developments in Anti-HIV Chemotherap.* Curr. Med. Chem. 2001 8:1543-1572) Two general classes of RTI inhibitors have been identified: nucleoside reverse transcriptase inhibitors (NRTI) and non-nucleoside reverse transcriptase inhibitors. Currently the CCR5 and CXCR4 co-receptors have emerged as a potential targets for anti-HIV-1 chemotherapy (D. Chantry, *Expert Opin. Emerg. Drugs* 2004 9(1):1-7; C. G. Barber, *Curr. Opin. Invest. Drugs* 2004 5(8):851-861; D. Schols, *Curr. Topics Med. Chem.* 2004 4(9):883-893; N. A. Meanwell and J. F. Ksadow, *Curr. Opin. Drug Discov. Dev.* 2003 6(4):451-461). N-substituted hydroxy pyrimidinone carboxamide inhibitors of HIV-1 integrase have been disclosed by B. Crescenzi et al. in WO2003/035077, published May 1, 2003, and MK-0518 is nearing approval NRTIs typically are 2',3'-dideoxynucleoside (ddN) analogs that must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity. (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423-1442; E. De Clercq, *The role of non-nucleoside reverse transcriptase inhibitors (NNRTIs) in the therapy of HIV infection*, Antiviral Res. 1998 38:153-179; E. De Clercq, *New Developments in Anti-HIV Chemotherapy*, Current Med. Chem. 2001 8(13): 1543-1572; G. Moyle, *The Emerging Roles of Non-Nucleoside Reverse Transcriptase Inhibitors in Antiviral Therapy*, Drugs 2001 61 (1):19-26) Although over thirty structural classes of NNRTIs have been identified in the laboratory, only three compounds have been approved for HIV therapy: efavirenz, nevirapine and delavirdine.

Initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3): 186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV-1.

Compounds of formula I wherein R$^3$ is H are efficacious HIVRT inhibitors however their utility is limited by limited bioavailability. Effective therapy for HIV-1 requires compounds that provide sustained high levels of compounds to minimize the opportunity for the emergence of resistant strains.

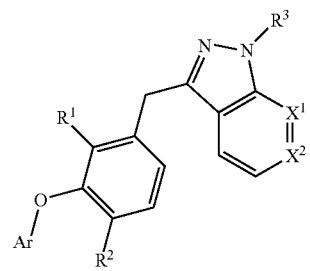

I

Compounds of formula I wherein $R^3$ is hydrogen or $C_{1-6}$ alkyl and $R^1$, $R^2$, $X^1$, $X^2$ and Ar are as defined in the Summary of the Invention have been described by J. Kennedy-Smith et al. in U.S. Publication No. 20080045511 which was filed Aug. 15, 2007 and which is hereby incorporated by reference in its entirety.

SUMMARY OF THE INVENTION

The present invention relates to compounds according to formula I wherein:

$X^1$ and $X^2$ are independently CH or N;

$R^1$ is fluorine or hydrogen;

$R^2$ is hydrogen, halogen, $C_{1-6}$ alkyl, $C_{3-7}$ cycloalkyl, $C_{1-6}$ haloalkyl, $C_{1-6}$ alkoxy, or $C_{1-6}$ alkylsulfonyl;

Ar is phenyl substituted with one to three groups independently selected in each occurrence from the group consisting of hydrogen, halogen, cyano, $C_{1-6}$ alkyl, $C_{1-6}$ alkoxy, $C_{1-6}$ haloalkyl and $C_{3-7}$ cycloalkyl;

$R^3$ is independently selected in each occurrence from the group consisting of:
(i) $CH_2OH$
(ii) $CH_2O-C(=O)(CH_2)_nCO_2R^4$ wherein n is 2 to 5;
(iii) $CH_2O-C(=O)CH_2OCH_2CO_2R^4$
(iv) $CH_2OCOR^{15}$;
(v) $CH_2OC(=O)CHR^6NH_2$;
(vi) $C(=O)R^5$; and,
(vii) $CH_2OP(=O)(OH)_2$;

$R^4$ is hydrogen or $C_{1-10}$ alkyl;

$R^5$ is hydrogen or $C_{1-10}$ alkyl, $C_{1-10}$ haloalkyl, $C_{1-10}$ aminoalkyl, $C_{1-3}$ alkylamino-$C_{1-10}$ alkyl, $C_{1-3}$ dialkylamino-$C_{1-10}$ alkyl, $C_{2-10}$ alkenyl, $C_{3-7}$ cycloalkyl, $C_{1-6}$ alkoxy, $C_{1-10}$ aminoalkoxy, $C_{1-3}$ alkylamino-$C_{1-10}$ alkoxyl, $C_{1-3}$ dialkylamino-$C_{1-10}$ alkoxy, $NR^{7a}R^{7b}$, phenyl or pyridinyl said phenyl or pyridinyl ring optionally independently substituted with 1 to 3 substituents selected from the group consisting of halogen, $C_{1-10}$ alkyl, $C_{1-3}$ alkoxy, nitro and cyano;

$R^6$ is $C_{1-6}$ alkyl or the side chain of a naturally occurring amino acid;

$R^{7a}$ and $R^{7b}$ are independently hydrogen, $C_{1-6}$ alkyl, $C_{1-10}$ aminoalkyl, $C_{1-3}$ alkylamino-$C_{1-10}$ alkyl, $C_{1-3}$ dialkylamino-$C_{1-10}$ alkyl; or pharmaceutically acceptable salts thereof.

Compounds of formula I inhibit HIVRT and afford a method for prevention and treatment of HIV-1 infections and the treatment of AIDS and/or ARC. Compounds of the present invention wherein $R^3$ is as described in this summary are rapidly and efficiently absorbed into the circulation and afford high levels of compounds with potent broad spectrum anti-HIV-1 activity. The present invention also relates to compositions containing compounds of formula I useful for the prevention and treatment of HIV-1 infections and the treatment of AIDS and/or ARC. The present invention further relates to compounds of formula I that are useful in monotherapy or combination therapy with other antiviral agents.

DETAILED DESCRIPTION OF THE INVENTION

Figure 1:
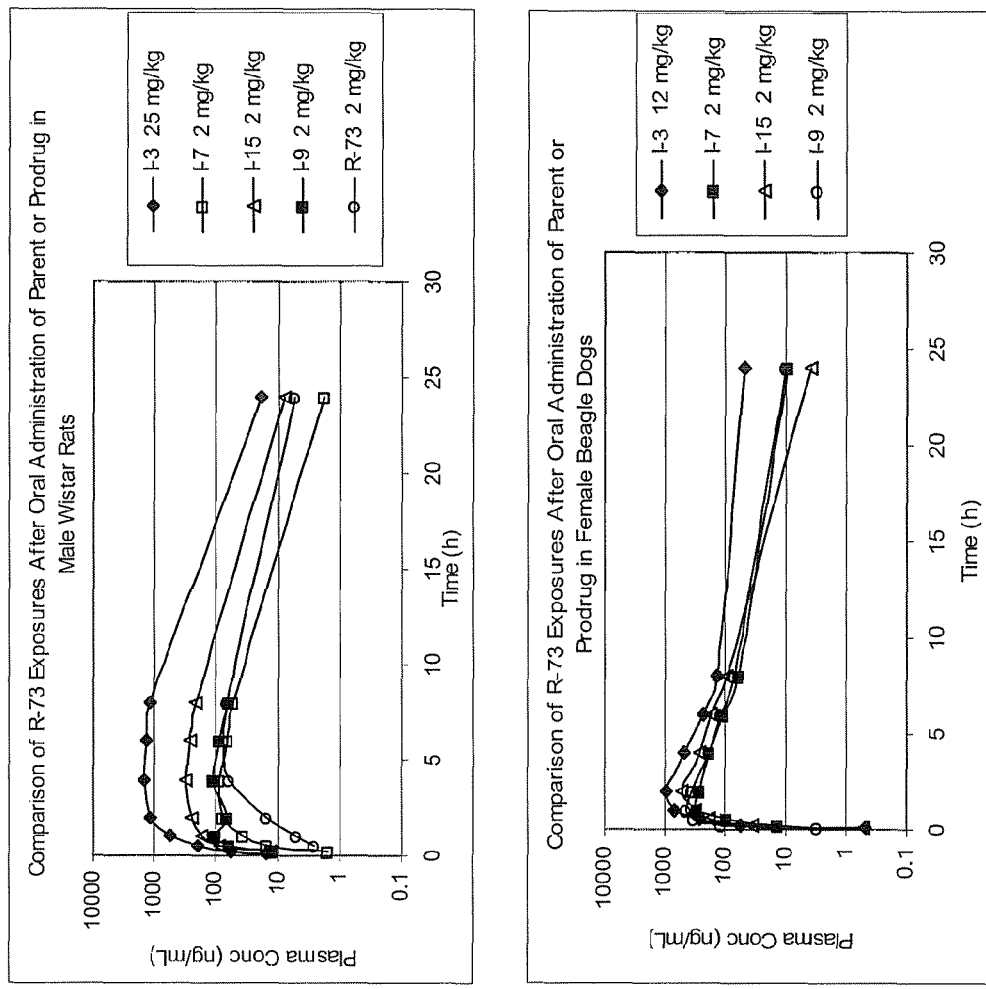
FIG. 1 graphically exemplifies the results of pharmacokinetic experiments comparing the bioavailability of four prodrugs of 3-[6-bromo-2-fluoro-3-(1H-pyrazolo[3,4-c]pyridazin-3-ylmethyl)-phenoxy]-5-chloro-benzonitrile (R-73) in rats and dogs.
Figure 2:
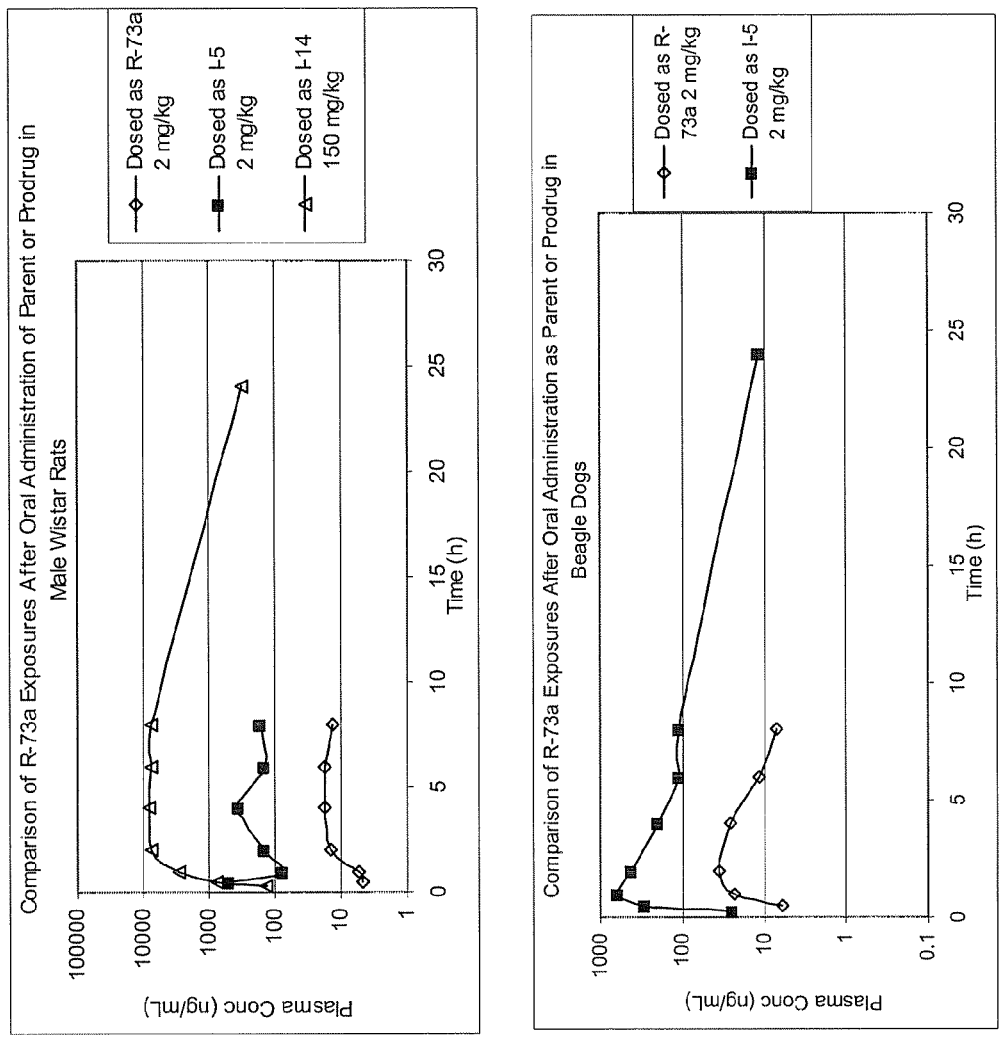
FIG. 2 graphically exemplifies the results of pharmacokinetic experiments comparing the bioavailability of four prodrugs of 3-chloro-5-[6-chloro-2-fluoro-3-(1H-pyrazolo[3,4-c]pyridazin-3-ylmethyl)-phenoxy]-benzonitrile (R-73a) in rats and dogs.
Figure 3:
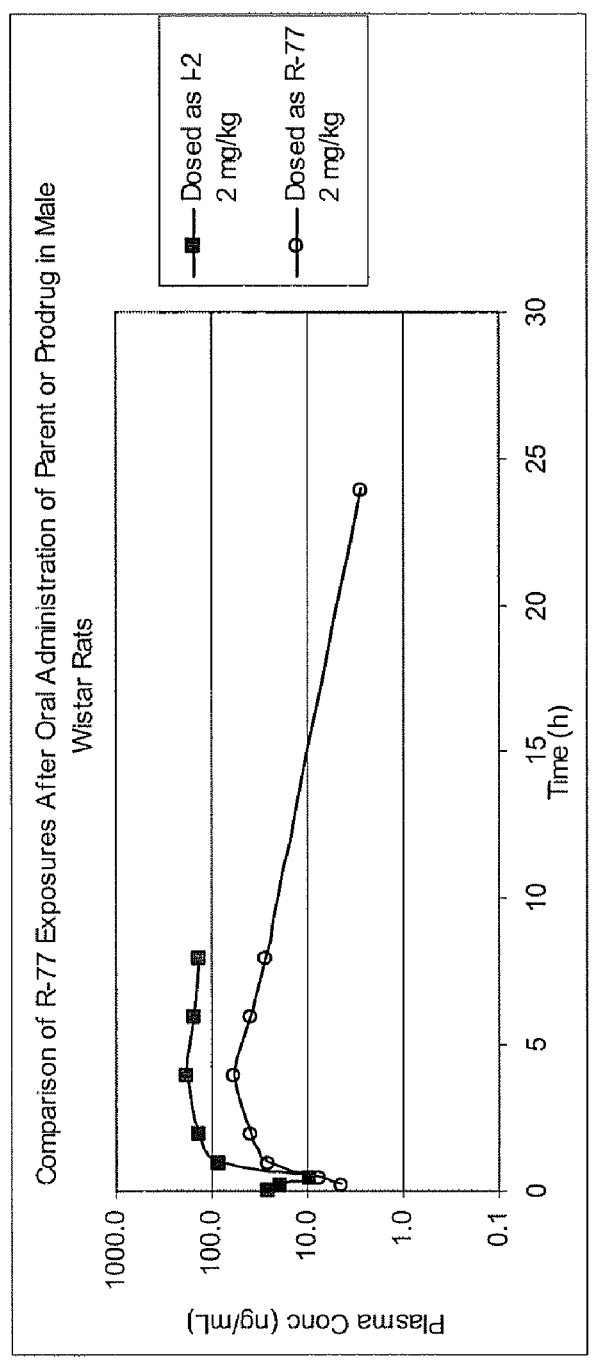
FIG. 3 provides graphs of the results of pharmacokinetic experiments comparing the bioavailability of a prodrug I-2 of 5-[6-bromo-2-fluoro-3-(1H-pyrazolo[3,4-c]pyridazin-3-ylmethyl)-phenoxy]-isophthalonitrile (R-77) in rats.

The compounds of formula I wherein $R^3$ is hydrogen are potent inhibitors of HIVRT with a broad spectrum of activity against mutant strains which are resistant to other nonnucleoside RT inhibitors. Effective antiviral therapy requires high levels of the active ingredient in the blood to minimize the emergence of resistant strains. Unfortunately the these compounds exhibit limited gastro-intestinal absorption. Secondly, suboptimal physical properties of the compounds restrict formulation options that could be employed to enhance delivery of the active ingredient.

Albert introduced the term prodrug to describe a compound which lacks intrinsic biological activity but which is capable of metabolic transformation to the active drug substance (A. Albert, *Selective Toxicity*, Chapman and Hall, London, 1951). Produgs have been recently reviewed (P. Ettmayer et al., *J. Med. Chem.* 2004 47(10):2393-2404; K. Beaumont et al., *Curr. Drug Metab.* 2003 4:461-485; H. Bundgaard, *Design of Prodrugs: Bioreversible derivatives for various functional groups and chemical entities in Design of Prodrugs*, H. Bundgaard (ed) Elsevier Science Publishers, Amersterdam 1985; G. M. Pauletti et al. *Adv. Drug Deliv. Rev.* 1997 27:235-256; R. J. Jones and N. Bischofberger, *Antiviral Res.* 1995 27; 1-15 and C. R. Wagner et al., *Med. Res. Rev.* 2000 20:417-45). While the metabolic transformation can catalyzed by specific enzymes, often hydrolases, the active compound can also be regenerated by non-specific chemical processes.

Pharmaceutically acceptable prodrugs refer to a compound, which frequently have limited or no inherent biologically active but which can be metabolized, for example hydrolyzed or oxidized, in the host to form the biologically active compound. Typical examples of prodrugs include compounds that have biologically labile protecting groups linked to a functional moiety of the active compound. Alkylation, acylation or other lipophilic modification of the parent compound have been utilized in the produce prodrugs with optimal physical compounds that efficiently revert to the parent compound.

Factors limiting oral bioavailability frequently are absorption from the gastrointestinal tract and first-pass excretion by the gut wall and the liver. Optimization of transcellular absorption through the GI tract requires a $D_{(7.4)}$ greater than zero. Optimization of the distribution coefficient does not, however, insure success. The prodrug may have to avoid active efflux transporters in the enterocyte. Intracellular metabolism in the enterocyte can result in passive transport or active transport of the metabolite by efflux pumps back into the gut lumen. The prodrug must also resist undesired biotransformations in the blood before reaching the target cells or receptors.

The quantity $D_{(7.4)}$ refers the distribution coefficient wherein the aqueous phase is buffered to pH 7.4. The distribution coefficient is the ratio of the sum of the concentrations of all forms of the compound (ionized plus unionized) in each of the two phases. Log D is defined as the logarithm of the ratio of the sum of concentrations of the solute's various forms in one solvent, to the sum of the concentrations of its forms in the other solvent.

While putative prodrugs sometimes can rationally envisioned based on the chemical functionality present in the molecule, finding a prodrug remains an empirical exercise. Predictions regarding the rate of, and product from, in vivo transformations is filled with uncertainty. Chemical modification of an active compound produces an entirely new molecular entity that can exhibit undesirable physical, chemical and biological properties absent in the parent compound. Regulatory requirements for identification of metabolites may pose challenges if multiple pathways lead to a plurality of metabolites. Thus, the identification of prodrugs remains an uncertain and challenging exercise. Moreover, evaluating pharmacokinetic properties of potential prodrugs is a challenging and costly endeavor. Pharmacokinetic results from animal models may be difficult to extrapolate to humans.

The object of the present invention is to provide new compounds, methods and compositions for the treatment of a host infected with HIV-1.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments which follow, substituents which can be present in each embodiment and which are not explicitly defined retain the broadest definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

It will be understood that the subject to which a compound of the invention is administered need not suffer from a specific traumatic state. Indeed, the compounds of the invention may be administered prophylactically, prior to any development of symptoms. The term "therapeutic", "therapeutically", and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

When any variable (e.g., $R^1$, $R^{4a}$, Ar, $X^1$ or Het) occurs more than one time in an constituent or in any formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

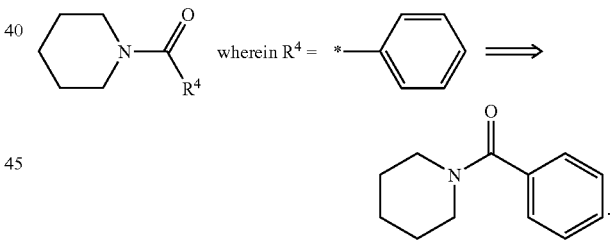

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

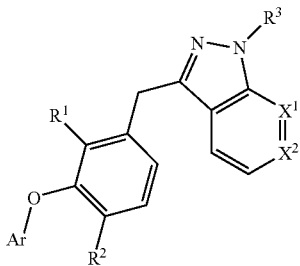

In one embodiment of the present invention there is provided a compound according to formula I wherein $R^1$, $R^2$, $R^3$, $R^4$, $R^5$, $R^6$, $R^{7a}$, $R^{7b}$, Ar, $X^1$, $X^2$ and n areas defined herein above and pharmaceutically acceptable salts thereof.

In a second embodiment of the present invention there is provided a compound according to formula I wherein $X^1$ is N; $X^2$ is CH. Substituent definitions in this and the following embodiments which are not specifically limited in the description of the embodiment retain the broadest scope defined in the Summary of the Invention. Furthermore all the embodiments include pharmaceutically acceptable salts of the compounds of formula I.

In a third embodiment of the present invention there is provided a compound according to formula I wherein $X^1$ is N; $X^2$ is CH; Ar is phenyl substituted with two groups independently selected in each occurrence from the group consisting of halogen, cyano and $C_{1-6}$ haloalkyl; $R^1$ is fluoro; and $R^3$ is selected from the group consisting of: (i) $CH_2O—C(=O)(CH_2)_nCO_2R^4$ wherein n is 2 to 5, (ii) $CH_2OCOR^5$, and, (iii) $C(=O)R^5$.

In a fourth embodiment of the present invention there is provided a compound according to formula I wherein $X^1$ is N; $X^2$ is CH; Ar is phenyl substituted with two groups independently selected in each occurrence from the group consisting of halogen, cyano and $C_{1-6}$ haloalkyl; $R^1$ is fluoro; and $R^3$ is $CH_2O—C(=O)(CH_2)_nCO_2R^4$; n is 2.

In a fifth embodiment of the present invention there is provided a compound according to formula I wherein $X^1$ is N; $X^2$ is CH; Ar is 3,5-dicyano-phenyl, 3-chloro-5-cyano-phenyl or 3-cyano-5-difluoromethyl-phenyl; $R^1$ is fluoro; R2 is bromo, chloro or $C_{1-6}$ alkyl; $R^3$ is selected $CH_2O—C(=O)(CH_2)_nCO_2R^4$ and n is 1 to 4.

In a sixth embodiment of the present invention there is provided a compound according to formula I wherein $X^1$ and $X^2$ are N.

In a seventh embodiment of the present invention there is provided a compound according to formula I wherein $X^1$ and $X^2$ are N; Ar is phenyl substituted with two groups independently selected in each occurrence from the group consisting of halogen, cyano and $C_{1-6}$ haloalkyl; $R^1$ is fluoro; and $R^3$ is selected from the group consisting of: (i) $CH_2O—C(=O)(CH_2)_nCO_2R^4$ wherein n is 2 to 5, (ii) $CH_2OCOR^5$, and, (iii) $C(=O)R^5$.

In a eighth embodiment of the present invention there is provided a compound according to formula I wherein $X^1$ and $X^2$ are N; Ar is phenyl substituted with two groups independently selected in each occurrence from the group consisting of halogen, cyano and $C_{1-6}$ haloalkyl; $R^1$ is fluoro; $R^3$ is $CH_2O—C(=O)(CH_2)_nCO_2R^4$; n is 2.

In a ninth embodiment of the present invention there is provided a compound according to formula I wherein $X^1$ and $X^2$ are N; Ar is 3,5-dicyano-phenyl, 3-chloro-5-cyano-phenyl or 3-cyano-5-difluoromethyl-phenyl; $R^1$ is fluoro; $R^2$ is chloro, bromo or $C_{1-6}$ alkyl; $R^3$ is $CH_2O—C(=O)(CH_2)_nCO_2R^4$ and n is 2 to 5.

In a tenth embodiment of the present invention there is provided a compound according to formula I selected from the group consisting of:

Succinic acid mono-{3-[4-bromo-3-(3-chloro-5-cyano-phenoxy)-2-fluoro-benzyl]-pyrazolo[3,4-b]pyridin-1-ylmethyl}ester;

Succinic acid mono-{3-[4-bromo-3-(3,5-dicyano-phenoxy)-2-fluoro-benzyl]-pyrazolo[3,4-b]pyridin-1-ylmethyl}ester;

Succinic acid mono-{3-[4-bromo-3-(3-chloro-5-cyano-phenoxy)-2-fluoro-benzyl]-pyrazolo[3,4-c]pyridazin-1-ylmethyl}ester;

Succinic acid mono-{3-[4-bromo-3-(3,5-dicyano-phenoxy)-2-fluoro-benzyl]-pyrazolo[3,4-c]pyridazin-1-ylmethyl}ester;

Succinic acid mono-{3-[4-chloro-3-(3-chloro-5-cyano-phenoxy)-2-fluoro-benzyl]-pyrazolo[3,4-c]pyridazin-1-ylmethyl}ester;

3-[4-Bromo-3-(3-chloro-5-cyano-phenoxy)-2-fluoro-benzyl]-pyrazolo[3,4-c]pyridazine-1-carboxylic acid methyl ester;

Pentanedioic acid mono-{3-[4-bromo-3-(3-chloro-5-cyano-phenoxy)-2-fluoro-benzyl]-pyrazolo[3,4-c]pyridazin-1-ylmethyl}ester;

Acetic acid 3-[4-bromo-3-(3-chloro-5-cyano-phenoxy)-2-fluoro-benzyl]-pyrazolo[3,4-c]pyridazin-1-ylmethyl ester;

(S)-2-Amino-3-methyl-butyric acid 3-[4-bromo-3-(3-chloro-5-cyano-phenoxy)-2-fluoro-benzyl]-pyrazolo[3,4-c]pyridazin-1-ylmethyl ester;

{3-[4-Bromo-3-(3-chloro-5-cyano-phenoxy)-2-fluoro-benzyl]-pyrazolo[3,4-c]pyridazin-1-ylmethoxycarbonyl-methoxy}-acetic acid;

3-[4-Bromo-3-(3-chloro-5-cyano-phenoxy)-2-fluoro-benzyl]-pyrazolo[3,4-c]pyridazine-1-carboxylic acid ethyl ester;

3-[4-Bromo-3-(3-chloro-5-cyano-phenoxy)-2-fluoro-benzyl]-pyrazolo[3,4-c]pyridazine-1-carboxylic acid isopropyl ester;

Succinic acid mono-{3-[4-chloro-3-(3,5-dicyano-phenoxy)-2-fluoro-benzyl]-pyrazolo[3,4-c]pyridazin-1-ylmethyl}ester;

3-[4-Bromo-3-(3-chloro-5-cyano-phenoxy)-2-fluoro-benzyl]-pyrazolo[3,4-c]pyridazine-1-carboxylic acid 2-dimethylamino-1-methyl-ethyl ester;

Pentanedioic acid mono-{3-[4-chloro-3-(3-chloro-5-cyano-phenoxy)-2-fluoro-benzyl]-pyrazolo[3,4-c]pyridazin-1-ylmethyl}ester;

Hexanedioic acid mono-{3-[4-bromo-3-(3-chloro-5-cyano-phenoxy)-2-fluoro-benzyl]-pyrazolo[3,4-c]pyridazin-1-ylmethyl}ester;

3-[3-(1-Acetyl-1H-pyrazolo[3,4-c]pyridazin-3-ylmethyl)-6-bromo-2-fluoro-phenoxy]-5-chloro-benzonitrile;

3-{6-Bromo-2-fluoro-3-[1-(pyridine-3-carbonyl)-1H-pyrazolo[3,4-c]pyridazin-3-ylmethyl]-phenoxy}-5-chloro-benzonitrile 3-[6-Bromo-2-fluoro-3-(1-isobutyryl-1H-pyrazolo[3,4-c]pyridazin-3-ylmethyl)-phenoxy]-5-chloro-benzonitrile;

3-[4-Bromo-3-(3-chloro-5-cyano-phenoxy)-2-fluoro-benzyl]-pyrazolo[3,4-b]pyridine-1-carboxylic acid (2-aminoethyl)-methyl-amide;

3-[4-Bromo-3-(3-chloro-5-cyano-phenoxy)-2-fluoro-benzyl]-pyrazolo[3,4-b]pyridine-1-carboxylic acid (2-aminoethyl)-amide;

Phosphoric acid mono-{3-[4-bromo-3-(3-chloro-5-cyanophenoxy)-2-fluoro-benzyl]-pyrazolo[3,4-b]pyridin-1-ylmethyl}ester; and, Phosphoric acid mono-{3-[4-bromo-3-(3-chloro-5-cyanophenoxy)-2-fluoro-benzyl]-pyrazolo[3,4-c]pyridazin-1-ylmethyl}ester.

In an eleventh embodiment of the present invention there is provided a method for treating an HIV-1 infection, or preventing an HIV-1 infection, or treating AIDS or ARC, comprising administering to a host in need thereof a therapeutically effective amount of a compound according to formula I wherein $R^1$, $R^2$, $R^3$, $R^4$, $R^5$, $R^6$, $R^{7a}$, $R^{7b}$, Ar, $X^1$, $X^2$ and n are as defined herein above.

In an twelfth embodiment of the present invention there is provided a method for treating an HIV-1 infection, preventing an HIV-1 infection, or treating AIDS or ARC, comprising co-administering to a host in need thereof a therapeutically effective amount of at least one compound selected from the group consisting of HIV protease inhibitors, nucleoside reverse transcriptase inhibitors, non-nucleoside reverse transcriptase inhibitors, integrase inhibitor, CCR5 antagonists and viral fusion inhibitors and a compound according to formula I wherein $R^1$, $R^2$, $R^3$, $R^4$, $R^5$, $R^6$, $R^{7a}$, $R^{7b}$, Ar, $X^1$, $X^2$ and n are as defined herein above.

In an thirteenth embodiment of the present invention there is provided a method for treating an HIV-1 infection, preventing an HIV-1 infection, or treating AIDS or ARC, comprising co-administering to a host in need thereof a therapeutically effective amount of at least one compound selected from the group consisting of zidovudine, lamivudine, didanosine, zalcitabine, stavudine, emtricibine, abacavir, tenofovir, efavirenz, nevirapine, delavirdine, etravirine, saquinavir, ritonavir, nelfinavir, indinavir, amprenavir, atazanavir, lopinavir, enfuvirtide, maraviroc and raltegravin along with a compound according to formula I wherein $R^1$, $R^2$, $R^3$, $R^4$, $R^5$, $R^6$, $R^{7a}$, $R^{7b}$, Ar, $X^1$, $X^2$ and n are as defined herein above.

In an fourteenth embodiment of the present invention there is provided a method for inhibiting HIVRT in a host infected with HIV-1 comprising administering to a host in need thereof a therapeutically effective amount of a compound according to formula I wherein $R^1$, $R^2$, $R^3$, $R^4$, $R^5$, $R^6$, $R^{7a}$, $R^{7b}$, Ar, $X^1$, $X^2$ and n are as defined herein above.

In an fifteenth embodiment of the present invention there is provided a method for inhibiting HIVRT in a host infected with HIV-1 wherein said HIVRT has at least one mutation compared to wild type HIVRT comprising administering to a host in need thereof a therapeutically effective amount of a compound according to formula I wherein $R^1$, $R^2$, $R^3$, $R^4$, $R^5$, $R^6$, $R^{7a}$, $R^{7b}$, Ar, $X^1$, $X^2$ and n are as defined herein above.

In an sixteenth embodiment of the present invention there is provided a method for inhibiting HIVRT in a host infected with HIV-1 wherein said HIVRT has at least one mutation compared to wild type HIVRT and which exhibits reduced sensitivity to nevirapine, delaviradine, efavirenz, and etravirine comprising administering to a host in need thereof a therapeutically effective amount of a compound according to formula I wherein $R^1$, $R^2$, $R^3$, $R^4$, $R^5$, $R^6$, $R^{7a}$, $R^{7b}$, Ar, $X^1$, $X^2$ and n are as defined hereinabove.

In a seventeenth embodiment of the present invention there is provided a pharmaceutical composition comprising a compound according to formula I and at least one pharmaceutically acceptable carrier, excipient or diluent.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically named group. Thus, for example, "phenylalkyl" denotes the radical R'R''-, wherein R' is a phenyl radical, and R'' is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene (—CH$_2$—) the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkenyl" as used herein denotes an unsubstituted hydrocarbon chain radical having from 2 to 10 carbon atoms having one or two olefinic double bonds [preferably one olefinic double bond]. $C_{2-10}$ alkenyl" as used herein refers to an alkenyl composed of 2 to 10 carbons. Examples are vinyl, 1-propenyl, 2-propenyl (allyl) or 2-butenyl (crotyl).

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "alkylsulfonyl" and "arylsulfonyl" as used herein denotes a group of formula —S(=O)$_2$R wherein R is alkyl or aryl respectively and alkyl and aryl are as defined herein.

The term "halogen" or "halo" as used herein means fluorine, chlorine, bromine, or iodine.

The term "cyano" as used herein refers to a carbon linked to a nitrogen by a triple bond, i.e., —C≡N. The term "nitro" as used herein refers to a group —NO$_2$.

The terms "aminoalkyl", "alkylaminoalkyl" and "dialkylaminoalkyl" as used herein refer to NH$_2$(alkylene)-, RHN(alkylene)-, and R$_2$N(alkylene)- respectively wherein R is alkyl, and both alkylene and alkyl are as defined herein. "C$_{1-10}$ alkylamino" as used herein refers to an aminoalkyl wherein alkyl is C$_{1-10}$. C$_{1-10}$ alkyl-amino-C$_{2-6}$ alkyl" as used herein refers to a C$_{1-10}$ alkylamino(alkylene)$_{2-6}$ wherein alkyl is C$_{1-10}$ and the alkylene is (CH$_2$)$_{2-6}$. When the alkylene group contains three or more carbon atoms, the alkylene can be linear, e.g. —(CH$_2$)$_4$— or branched, e.g., —(CMe$_2$CH$_2$)—.

The term "naturally occurring amino acids" as used herein means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Unless specifically indicated, all amino acids referred to in this application are in the L-form. The term "hydrophobic amino acid" as used herein glycine, alanine, valine, leucine, isoleucine, methionine, phenylalanine, tryptophan, and proline. The side chains of naturally occurring amino acids, which are used without implying any stereochemical configuration at the point of attachment to the remainder of the molecule, include: hydrogen, methyl, iso-propyl, iso-butyl, sec-butyl, —CH$_2$OH, —CH(OH)CH$_3$, —CH$_2$SH, —CH$_2$CH$_2$SMe, —(CH$_2$)$_p$COR wherein R is —OH or —NH$_2$ and p is 1 or 2, —(CH$_2$)$_q$—NH$_2$ where q is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene.

A-M. Vandamme et al. (*Antiviral Chemistry & Chemotherapy*, 1998 9:187-203) disclose current HAART clinical treatments of HIV-1 infections in man including at least triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. While HAART has dramatically altered the prognosis for HIV infected persons, there remain many drawbacks to the current therapy including highly complex dosing regimes and side effects that can be very severe (A. Carr and D. A. Cooper, *Lancet* 2000 356(9239):1423-1430). Moreover, these multidrug therapies do not eliminate HIV-1 and long-term treatment usually results in multidrug resistance, thus limiting their utility in long-term therapy. Development of new therapeutics which can be used in combination with NRTIs, NNRTIs, PIs and viral fusion inhibitors to provide better HIV-1 treatment remains a priority.

Typical suitable NRTIs include zidovudine (AZT; RETROVIR®); didanosine (ddI; VIDEX®); zalcitabine (ddC; HIVID®); stavudine (d4T; ZERIT®); lamivudine (3TC; EPIVIR®); abacavir (ZIAGEN®); adefovir dipivoxil [bis-(POM)-PMEA; PREVON®]; lobucavir (BMS-1 80194), a nucleoside reverse transcriptase inhibitor disclosed in EP-0358154 and EP-0736533; BCH-10652, a reverse transcriptase inhibitor (in the form of a racemic mixture of BCH-10618 and BCH-10619) under development by Biochem Pharma; emitricitabine [(−)-FTC] in development by Triangle Pharmaceuticals; β-L-FD4 (also called β-L-D4C and named β-L-2',3'-dicleoxy-5-fluoro-cytidene) licensed Vion Pharmaceuticals; DAPD, the purine nucleoside, (−)-β-D-2,6-diamino-purine dioxolane disclosed in EP-0656778 and licensed to Triangle Pharmaceuticals; and lodenosine (FddA), 9-(2,3-dideoxy-2-fluoro-β-D-threo-pentofuranosyl) adenine, an acid stable purine-based reverse transcriptase inhibitor under development by U.S. Bioscience Inc.

Typical suitable NNRTIs include nevirapine (BI-RG-587; VIRAMUNE®); delaviradine (BHAP, U-90152; RESCRIPTOR®); efavirenz (DMP-266; SUSTIVA®); and etravirine (TMC-125, INTELENCE®). Other NNRTIs under investigation include, but are not limited to PNU-142721, a furopyridine-thio-pyrimidine under development by Pfizer; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxy-methyl)-5-(1-methylethyl)-6-(phenylmethyl)-(2, 4(1H, 3H)-pyrimidinedione); and (+)-calanolide A (NSC-675451) and B, coumarin derivatives disclosed in U.S. Pat. No. 5,489,697.

Typical suitable PIs include saquinavir (Ro 31-8959; INVIRASE®; FORTOVASE®); ritonavir (ABT-538; NORVIR®); indinavir (MK-639; CRIXIVAN®); nelfnavir (AG-1343; VIRACEPT®); amprenavir (141W94; AGENERASE®); lasinavir (BMS-234475); DMP-450, a cyclic urea under development by Triangle Pharmaceuticals; BMS-2322623, an azapeptide under development by Bristol-Myers Squibb as a 2nd-generation HIV-1 PI; ABT-378 under development by Abbott; and AG-1549 an imidazole carbamate under development by Agouron Pharmaceuticals, Inc.

Other antiviral agents include hydroxyurea, ribavirin, IL-2, IL-12, pentafuside. Hydroxyurea (Droxia), a ribonucleoside triphosphate reductase inhibitor shown to have a synergistic effect on the activity of didanosine and has been studied with stavudine. IL-2 (aldesleukin; PROLEUKIN®) is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314. Pentafuside (FUZEON®) a 36-amino acid synthetic peptide that inhibits fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Ribavirin, 1-β-D-ribofuranosyl-1H-1,2,4-triazole-3-carboxamide.

The term "carboxy C$_{1-7}$ alkyl" or "C$_{1-7}$ carboxyalkyl" or denotes a C$_{1-7}$ alkyl group as defined above wherein at least one of the hydrogen atoms of the alkyl group is replaced by a carboxyl group Commonly used abbreviations include: acetyl (Ac), atmospheres (Atm), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylethylamine (DIPEA), di-iso-propylazodicarboxylate (DIAD), di-iso-butylaluminumhydride (DIBAL or DIBAL-H), N,N-dimethyl acetamide (DMA), 4-N,N-dimethylaminopyridine (DMAP), N,N-dimethylformamide (DMF), 1-(3-dimethylaminopropyl)-3-ethylcarbodiimide hydrochloride (EDCI), dimethyl sulfoxide (DMSO), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), tert-butyldimethylsilyl or $t\text{-}BuMe_2Si$ (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), $4\text{-}Me\text{-}C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| No. | Structure | ms | mp |
|-----|-----------|----|----|
| I-1 | 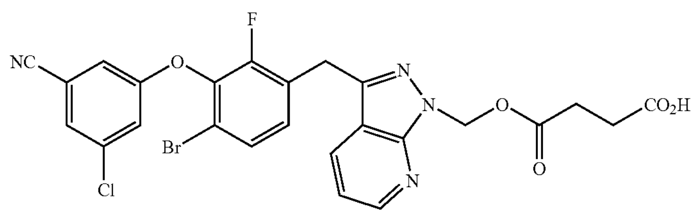 | 585 (M − H) | 183-184 |
| I-2 | 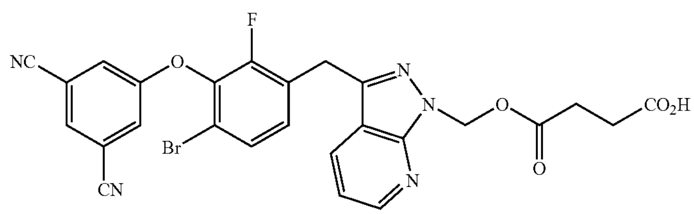 | 577.0397 | |
| I-3 | 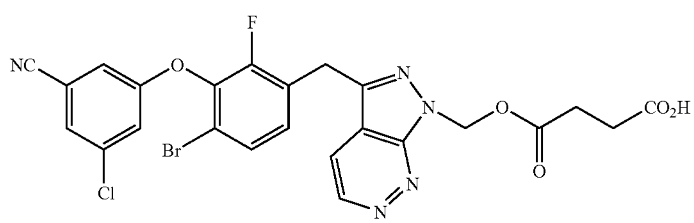 | | 172.6-173.9 |
| I-4 | 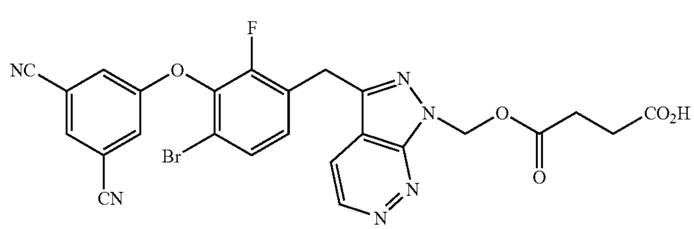 | | 175.2-176.5 |

TABLE 1-continued

| No. | Structure | ms | mp |
|---|---|---|---|
| I-5 | 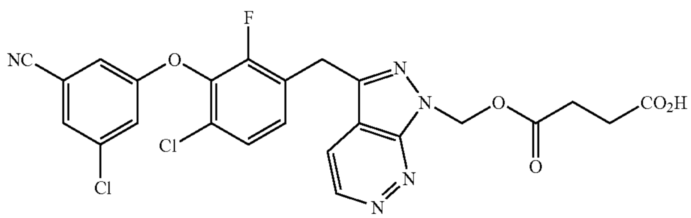 | | 173.0-174.8 |
| I-6 | 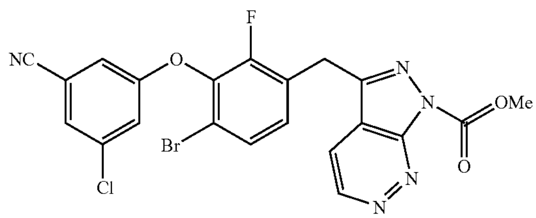 | 516, 518 [M + H] | 164.0-165.0 |
| I-7 | 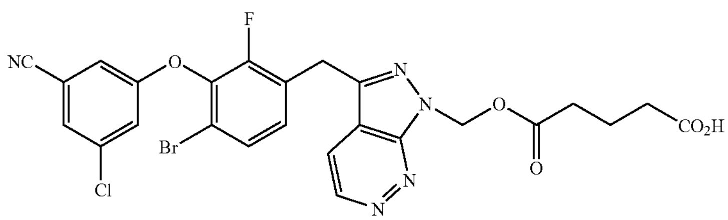 | | 149.8-150.7 |
| I-8 | 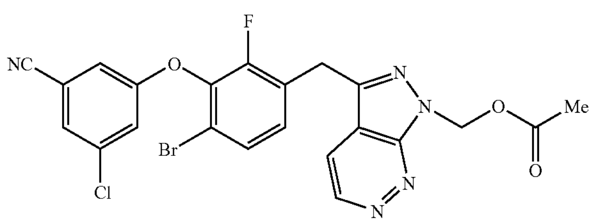 | 530, 532 [M + H] | 71.1-73.0 |
| I-9 | 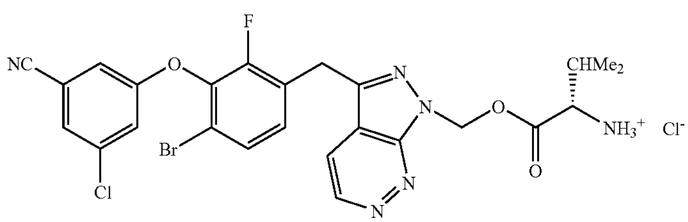 | | 155.0-156.0 |
| I-10 | 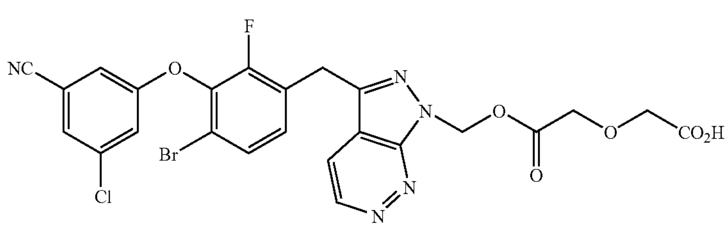 | | 146.0-147.0 |
| I-11 | 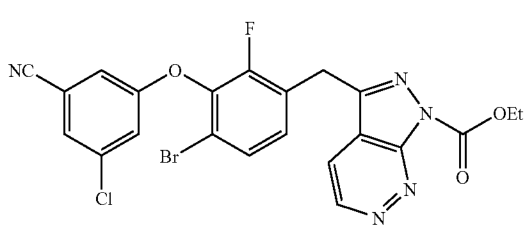 | | 139.0-140.0 |

TABLE 1-continued

| No. | Structure | ms | mp |
|---|---|---|---|
| I-12 | 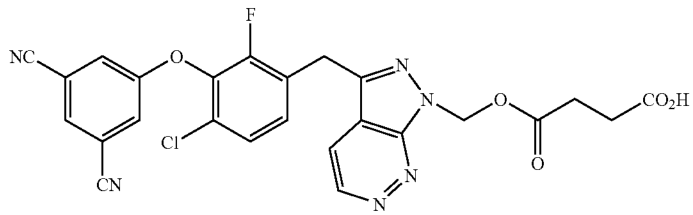 | | 166.1-169.9 |
| I-13 | 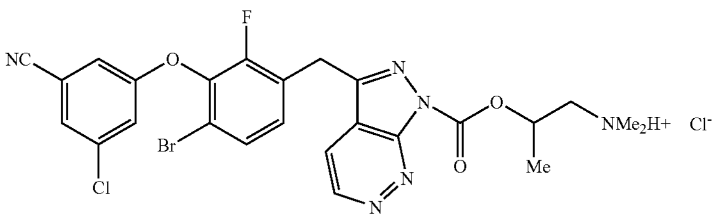 | | 119.0-122.0 |
| I-14 | 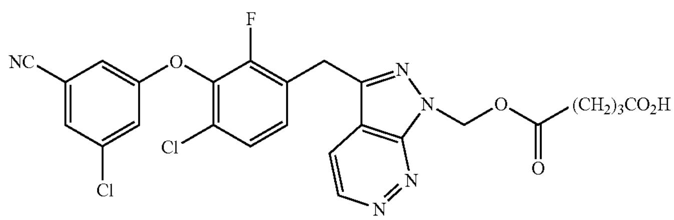 | | 176.0-178.0 |
| I-15 | 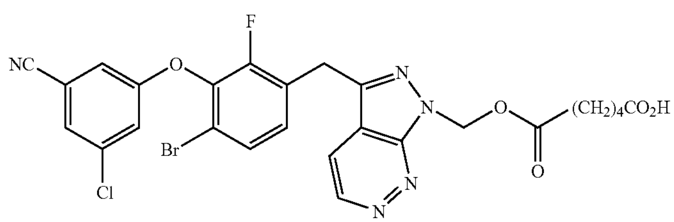 | | 159.0-160.0 |
| I-16 | 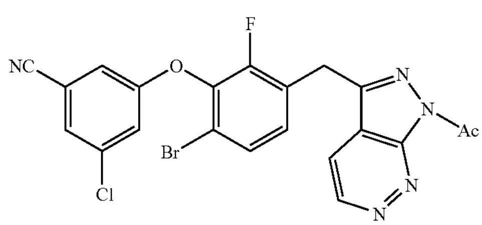 | 500, 502 [M + H] | 195.5-196.9 |
| I-17 | 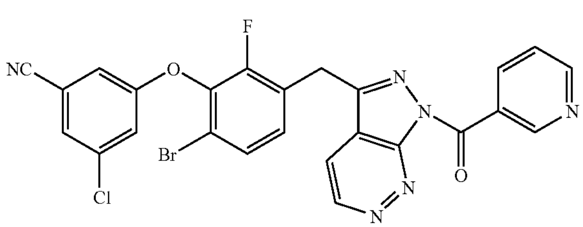 | 563, 565 [M + H] | 187.7-188.5 |
| I-18 | 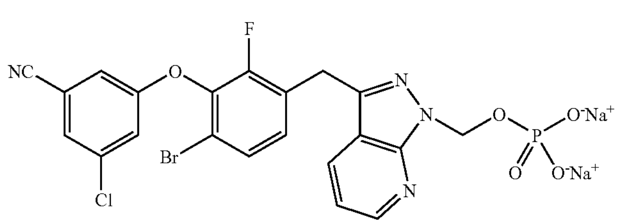 | | |

TABLE 1-continued

| No. | Structure | ms | mp |
|---|---|---|---|
| I-19 | 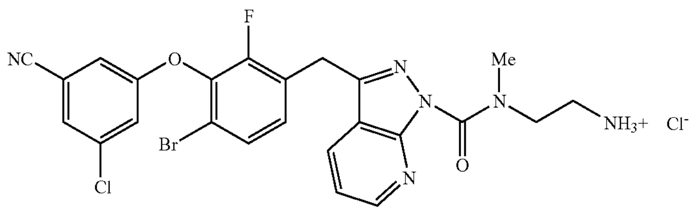 | 599 [M + H] | |
| I-20 | 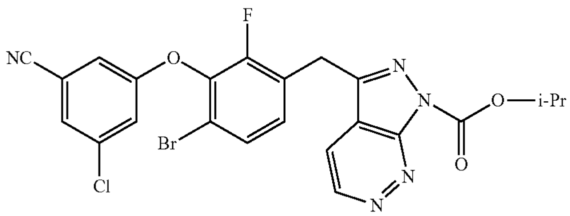 | | 166.1-166.9 |
| I-21 | 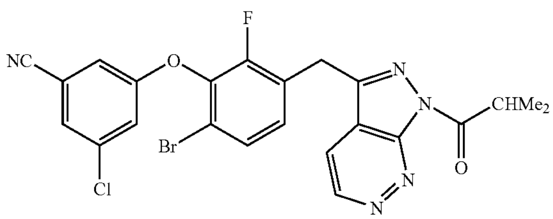 | | 157.7-159.3 |
| I-22 | 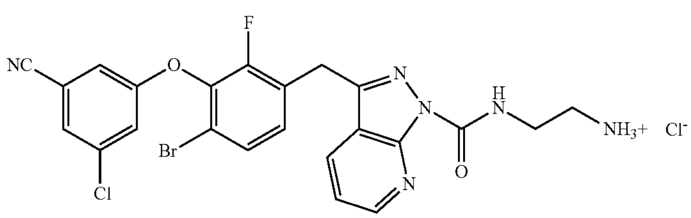 | 542.0269 | |

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

SCHEME A

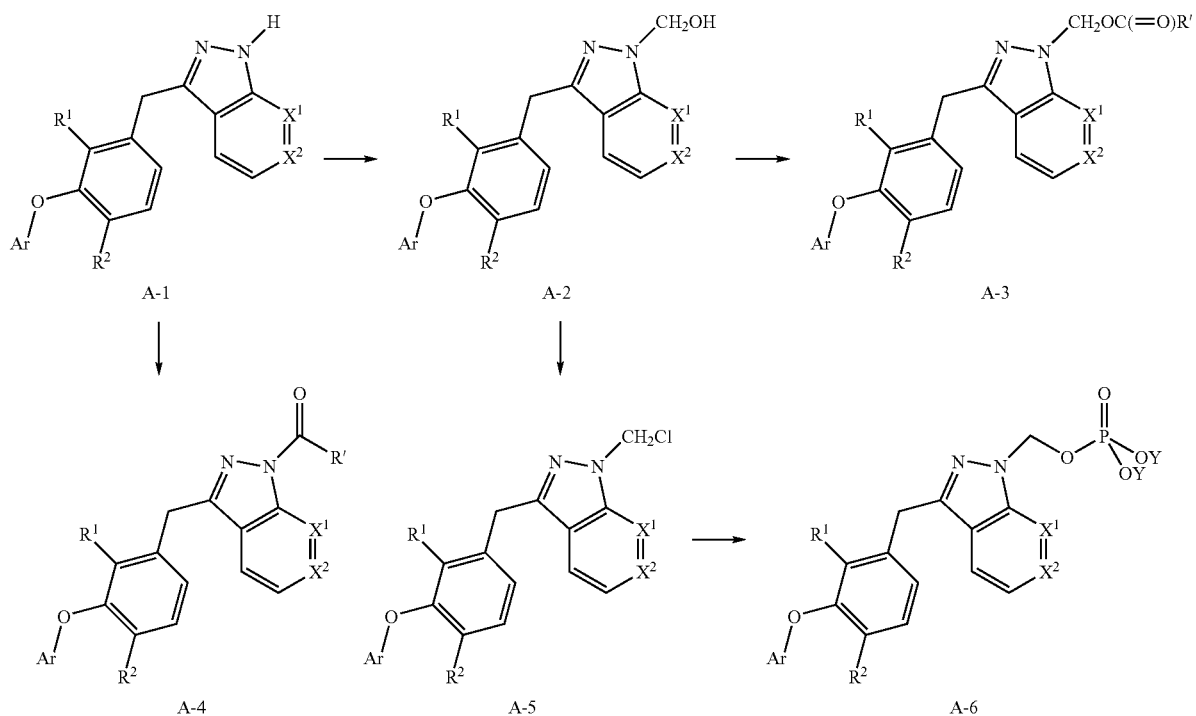

N-Acyloxymethyl derivatives (A-3) of compounds according to formula I are prepared by treating a fused pyrazole with formaldehyde to form the alcohol A-2 which is then acylated with an acyl halide, an anhydride or an activated carboxylic acid derivative to afford A-3 wherein R' is carboxy-$C_{2-5}$ alkyl, $C_{1-10}$ alkyl, $C_{1-10}$ haloalkyl, $C_{1-10}$ aminoalkyl, $C_{1-3}$ alkylamino-$C_{1-10}$ alkyl, $C_{1-3}$ dialkylamino-$C_{1-10}$ alkyl, $C_{2-10}$ alkenyl, $C_{3-7}$ cycloalkyl, $C_{1-6}$ alkoxy, $C_{1-10}$ aminoalkoxy, $C_{1-3}$ alkylamino-$C_{1-10}$ alkoxyl, $C_{1-3}$ dialkylamino-$C_{1-10}$ alkoxy, $NR^{7a}R^{7b}$, optionally substituted phenyl or optionally substituted pyridinyl or C(=O)R' comprise an alpha-amino acid. N-Acyl derivatives (A-4) are prepared similarly except the formaldehyde treatment is omitted and the pyrazole nitrogen is acylated with an acyl halide, an anhydride or an activated carboxylic acid derivative. Phosphoryloxymethyl derivatives (A-6) were prepared from the corresponding chloromethyl compound (A-5) by displacement with a dialkylphosphoric acid diester to afford A-6 wherein Y is alkyl which is further dealkylated to afford A-6 wherein Y is hydrogen, an alkali or alkaline cationic salt. The requisite pyrazoles of formula A-1 which are precursors have been described by J. Kennedy-Smith et al in U.S. Ser. No. 11/893,349 filed Aug. 15, 2007 and which is hereby incorporated by reference in its entirety. Procedures to prepare compounds according to formula A-1 can be found in the referential examples contained herein.

Activated carboxylic acids which can be used to prepared compounds of the present invention have been extensively researched for peptide coupling reactions and any of the plurality of alternatives would be suitable. The hydroxymethyl phosphate derivatives are prepared from the corresponding chloromethyl derivative which is treated with a dialkyl phosphate to afford the corresponding dialkyl phosphonate which is dealkylated to produce compounds of the present invention.

Biological Assays

The capacity for fused-pyrazoles (A-1) which are produced in vivo to inhibit HIVRT can be determined by the enzyme inhibition assay disclosed in example 9. The problem to be solved is to deliver sufficient HIV-1 transcriptase inhibitor to block viral replication and suppress the formation of resistant strains. The pharmacokinetic assays in examples 10 and 11 are used to evaluate the level of pyrazoles which are formed in the systemic circulation following an oral dose of the prodrug.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

"Pharmaceutically acceptable" means that the moiety is useful in preparing a pharmaceutical composition that is generally safe, non-toxic, and neither biologically nor otherwise undesirable.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor, a protease inhibitor, an integrase inhibitor or a $CCR_5$ or $CXCR_4$ antagonist. In addition compounds which block viral docking to CD4 have be identified and which may be used with compounds of the present invention. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent. Furthermore, treatment of a HIV-1 infection, as used herein, also includes treatment or prophylaxis of a disease or a condition associated with or mediated by HIV-1 infection, or the clinical symptoms thereof.

Example 1

Succinic acid mono-{3-[4-bromo-3-(3-chloro-5-cyano-phenoxy)-2-fluoro-benzyl]-pyrazolo[3,4-b]pyridin-1-ylmethyl}ester (I-1)

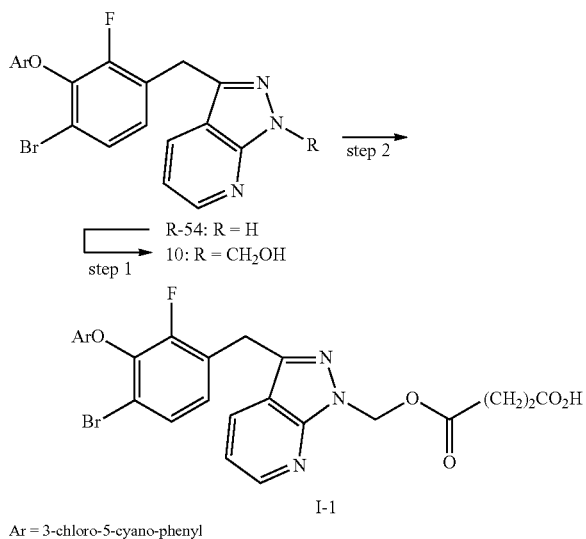

step 1—A mixture of R-54 (1.6 g), 37% aqueous formaldehyde solution and MeOH was stirred overnight at 60° C. under an inert atmosphere. The MeOH was evaporated and the resulting solution diluted with $H_2O$ and the resulting precipitate was filtered, washed with $H_2O$ and air-dried to afford 1.63 g of 10.

step 2—To a suspension of 10 (0.488, 1 mmol), succinic anhydride (0.15 g, 1.5 mmol), DMAP (6.1 mg, 0.05 mmol) and DCM (10 mL) at RT was added DIPEA (0.28 mL, 1.63 mmol) and the resulting mixture was stirred at RT. The solution became homogenous in 10 min. After 1 h the reaction was diluted with additional DCM (20 mL) and washed with 10% aq HCl, dried ($MgSO_4$), filtered and evaporated. The gummy residue was triturated EtOAc and sonicated which afforded a white powder which was filtered, washed with EtOAc and dried to afford 0.4 g of I-1. An additional 0.1 g was recovered in a second crop from the mother liquor: Anal. Calcd. for $C_{25}H_{17}BrClFN_4O_5$: C, 51.09; H, 2.92; N, 9.53. Found: C, 51.01; H, 2.93; N, 9.52.

I-2 was prepared analogously except in step 1, 5-[6-bromo-2-fluoro-3-(1H-pyrazolo[3,4-c]pyridazin-3-ylmethyl)-phenoxy]-isophthalonitrile (R-58) was used in place of R-54.

Example 2

Succinic acid mono-{3-[4-bromo-3-(3-chloro-5-cyano-phenoxy)-2-fluoro-benzyl]-pyrazolo[3,4-c]pyridazin-1-ylmethyl}ester (I-3)

step 1—A suspension of 3-[6-bromo-2-fluoro-3-(1H-pyrazolo[3,4-c]pyridazin-3-ylmethyl)-phenoxy]-5-chloro-benzonitrile (R-73, 1.32 g, 2.88 mmol), 37% aqueous formaldehyde (100 mL) and MeOH (100 mL) was stirred at 67° C. for 35 h. The volatile solvents were evaporated and the residue diluted with $H_2O$ and the resulting precipitate filtered, washed with $H_2O$ and air-dried to afford 1.27 g of 3-[6-bromo-2-fluoro-3-(1-hydroxymethyl-1H-pyrazolo[3,4-c]pyridazin-3-ylmethyl)-phenoxy]-5-chloro-benzonitrile (12).

step 2—A mixture of 12 (1.28 g, 2.62 mmol), succinic anhydride (0.39 g, 3.93 mmol), DMAP (16 mg, 0.13 mmol), DIPEA (0.73 mL, 4.19 mmol) and DCM (65 mL) was stirred at RT under an inert atmosphere for 3 h. The volatile solvents were evaporated and the crude residue was purified by $SiO_2$ chromatography eluting with a MeOH/DCM gradient (1 to 4% MeOH) to afford 0.75 g of I-3 as a brown solid which was dried overnight in vacuo at 110° C.: Anal. Calcd. for $C_{24}H_{16}BrClFN_5O_5$: C, 48.29; H, 2.85; N, 11.73. Found: C, 48.31; H, 2.68; N, 11.57.

I-4 is prepared analogously except in step 1, R-73 was replaced with 5-[6-bromo-2-fluoro-3-(1H-pyrazolo[3,4-c]pyridazin-3-ylmethyl)-phenoxy]-isophthalonitrile (R-77).

I-5 is prepared analogously except in step 1, R-73 was replaced with 5-[6-chloro-2-fluoro-3-(1H-pyrazolo[3,4-c]pyridazin-3-ylmethyl)-phenoxy]-5-chloro-benzonitrile (R-73a).

I-7 was prepared analogously except in step 2, succinic anhydride was replaced by dihydro-pyran-2,6-dione (glutaric anhydride).

I-10 was prepared analogously except in step 2, succinic acid was replaced with 1,4-dioxane-2,6-dione (CASRN 4480-83-5)

I-12 is prepared analogously except in step 1, R-73 was replaced with 5-[6-chloro-2-fluoro-3-(1H-pyrazolo[3,4-c]pyridazin-3-ylmethyl)-phenoxy]-isophthalonitrile (R-73b).

I-14 was prepared analogously except in step 1, R-73 was replaced with 3-[6-chloro-2-fluoro-3-(1H-pyrazolo[3,4-c]pyridazin-3-ylmethyl)-phenoxy]-5-chloro-benzonitrile (R-73a) and in step 2, succinic anhydride was replaced with glutaric anhydride.

I-15 was prepared analogously except in step 2, succinic anhydride was replace with 2,7-oxepanedione (adipic anhydride, CASRN 2035-75-8)

Example 3

Acetic acid 3-[4-bromo-3-(3-chloro-5-cyano-phenoxy)-2-fluoro-benzyl]-pyrazolo[3,4-c]pyridazin-1-ylmethyl ester (I-8)

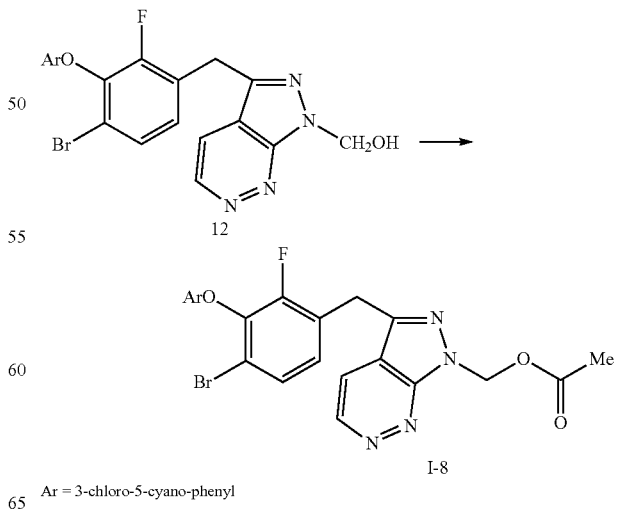

To a solution of 12 (0.1 g, 0.2 mmol) and DCM (3 mL) was added pyridine (0.08 mL, 1.0 mmol) and acetic anhydride (612 mg, 6 mmol). The resulting solution was stirred overnight at RT under an inert atmosphere. Starting material was still evident and additional aliquots of pyridine (0.08 mL) and Ac$_2$O (0.612 g) were added and the resulting mixture stirred at 55° C. for ca. 5 h. The volatile contents were evaporated and the residue purified in two batches on a preparative SiO$_2$ TLC plate developed with 60% EtOAc/hexane containing 1% TEA. The product was eluted from the plate and crystallized from DCM/hexane to afford 0.076 g of I-8: Anal. Calcd. for C$_{22}$H$_{14}$BrClFN$_5$O$_3$: C, 49.79; H, 2.66; N, 13.20. Found: C, 49.87; H, 2.63; N, 12.92.

Example 4

(S)-2-Amino-3-methyl-butyric acid 3-[4-bromo-3-(3-chloro-5-cyano-phenoxy)-2-fluoro-benzyl]-pyrazolo[3,4-c]pyridazin-1-ylmethyl ester; hydrochloride salt (I-9)

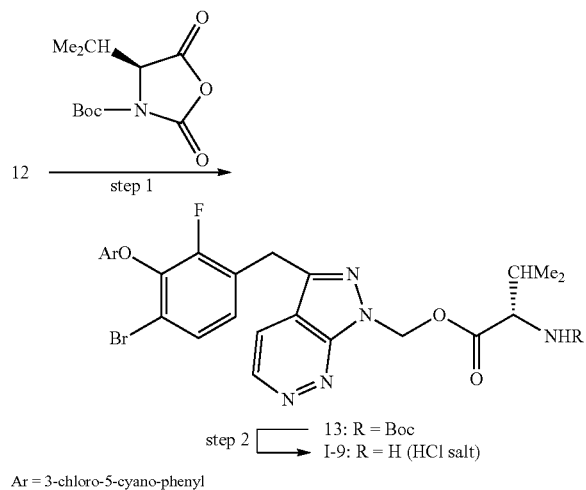

step 1—To a solution of 12 (0.200 g, 0.4 mmol) and anhydrous DMF (5 mL) was added TEA (0.2 equiv.) and (S)-valine-N-carboxyanhydride (0.117 g, 0.48 mmol). The resulting solution was stirred at RT for 2 h. The resulting solution was partitioned between equal volumes of EtOAc and H$_2$O and the EtOAc phase was separated. The aqueous phase was extracted with EtOAc and the combined extracts were dried (MgSO$_4$), filtered and evaporated. The crude product was purified on a preparative TLC plate developed with 3.5% MeOH/DCM containing 1% TEA which afford 250 mg of 13 as a viscous yellow oil.

step 2—To a vial which was flushed with a stream of Ar containing 13 (55 mg, 0.07 mmol), Et$_2$O (1 mL) and a stir bar was added 1.0 M HCl/Et$_2$O (0.21 mL). The Ar line was removed, the vial capped and stirred for 3.5 h. The solid was centrifuged down and the liquid decanted. The solid was twice suspended in EtOAc/hexane, centrifuged and the liquid decanted. The sample still contained some starting material and the process was repeated except ad additional aliquot of HCl/dioxane (2.5 equiv.) was added and the solution stirred for 6 h. A second 50 mg batch was prepared similarly and the products combined. The crude product was dried in a vacuum oven to afford 64 mg of I-9.

Example 5

3-[4-Bromo-3-(3-chloro-5-cyano-phenoxy)-2-fluoro-benzyl]-pyrazolo[3,4-c]pyridazine-1-carboxylic acid methyl ester (I-6)

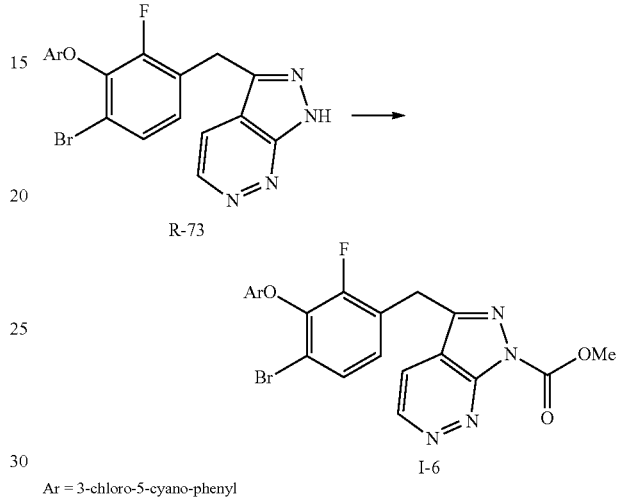

To a solution of R-73 (0.200 g, 0.44 mmol) in anhydrous THF (10 mL) was added Me$_3$SiCN (0.19 mL, 1.54 mmol) followed by 0.95 mL of a solution of methyl chloroformate (0.105 g) and MeCN (2 mL). The resulting solution was stirred at RT for 1 h. The reaction mixture was partitioned between H$_2$O and EtOAc and the aqueous layer was separated and extracted again with EtOAc. The combined extracts were dried (MgSO$_4$), filtered, evaporated and EtOAc/hexane was added resulting in a solid precipitate. The solid was repeated triturated with Et$_2$O/hexane which afford 0.061 of I-6 as a yellow solid which was dried overnight in a vacuum oven.

I-9 and I-20 were prepared analogously except methyl chloroformate was replaced with ethyl chloroformate and iso-propyl chloroformate respectively.

Example 6

3-[3-(1-Acetyl-1H-pyrazolo[3,4-c]pyridazin-3-ylmethyl)-6-bromo-2-fluoro-phenoxy]-5-chloro-benzonitrile (I-16)

To a solution of R-73 (0.050 g, 0.11 mmol) and dry MeCN (3 mL) was added Me$_3$SiCN (0.1 mL, 7 equivalents) and acetyl chloride (0.013 g, 0.48 mL of a solution of 27 mg of AcCl and 1.0 mL of MeCN). After stirring at RT for 15 min H$_2$O (20 mL), EtOAc (30 mL) and 5% aq NaHCO$_3$ (5 mL) were added sequentially. The EtOAc phase was separated and evaporated. The residue was taken up in DCM, dried (MgSO$_4$), filtered and evaporated and the product purified by re-crystallization from DCM/hexanes to affords 0.39 g of I-16 as a light brown powder.

3-{6-Bromo-2-fluoro-3-[1-(pyridine-3-carbonyl)-1H-pyrazolo[3,4-c]pyridazin-3-ylmethyl]-phenoxy}-5-chloro-benzonitrile was prepared analogously except acetyl chloride was replaced with nicotinoyl chloride to afford I-17: Anal. Calcd. for $C_{25}H_{13}BrClFN_6O_2$: C, 53.26; H, 2.32; N, 14.91. Found: C, 53.31; H, 2.22; N, 14.72.

Example 7

3-[4-Bromo-3-(3-chloro-5-cyano-phenoxy)-2-fluoro-benzyl]-pyrazolo[3,4-b]pyridine-1-carboxylic acid (2-amino-ethyl)-methyl-amide; hydrochloride salt (I-19)

step 1—An oven-dried vial was charged with DIPEA (0.44 mL, 2.5 mmol), tert-butyl-2-(methylamino)ethyl carbamate (132.4 mg, 0.76 mmol, CASRN 122734-32-1) and DCM (2 mL). An oven-dried microwave flask was charged with bis-trichloromethylcarbonate (0.090 g) and DCM (4 mL) and cooled to 0° C. The former solution was added to the cooled carbonated solution via syringe over ca. 2 min and stirred at 0° for 5 min and allowed to warm to RT. To the resulting solution was added R-54 (0.350 g) followed by pyridine (0.2 mL). The resulting mixture was heated in a sealed tube at 70° C. for ca. 16 h. The solid material was filtered. Both the solid and the filtrate contained starting material and the desires urea. The crude product was purified using three preparative tlc plates which were developed with 75% EtOAc/hexane. The recovered product from the plates was applied to another preparative tlc plate and sequentially developed with 45% EtOAc/hexane then 50% EtOAc/hexane then eluted from the plate. The resulting product was triturated with $Et_2O$/hexane and filtered to afford 0.018 g of the corresponding Boc urea (14).

step 2—To a solution of 14 (0.035 g, 0.053 mmol), DCM (2 mL), EtOAc (6 drops) and MeOH (3 drops) was added 1 M HCl/$Et_2O$ (0.13 mL) and stirred for 1 h before an additional aliquot of 1 M HCl/$Et_2O$ was added. After 1 h little reaction was apparent and 1M HCl/dioxane (0.1 mL) was added. After stirring for 1 h, the volatile solvents were evaporated and the residue triturated with $Et_2O$/hexane (1:1), filtered and dried in a vacuum oven to afford 31 mg of I-19 as a white powder.

Example 8

3-[4-Bromo-3-(3-chloro-5-cyano-phenoxy)-2-fluoro-benzyl]-pyrazolo[3,4-c]pyridazine-1-carboxylic acid 2-dimethylamino-1-methyl-ethyl ester; hydrochloride salt (I-13)

step 1—In an oven-dried vial was mixed 1-dimethylamino-2-propanol (0.73 mL, 6 mmol), dry pyridine (0.5 mL, 0.5 equiv.) and DCM (2.5 mL). A second oven-dried flask was charged with phosgene (0.6 mL, 1 equiv., 20% solution in toluene) and dry DCM (10 mL) and the solution was maintained under $N_2$ and cooled to −40° C. The contents of the vial were added dropwise and the resulting solution was stirred at −40° C. for 5 min then allowed to warm to RT. To the resulting solution was added R-73 (0.225 g, 0.49 mmol) and the resulting mixture stirred for 3 h. The solution was diluted with $Et_2O$ and the liquid phase decanted from the resulting precipitate. The solid was washed twice with $Et_2O$ (2×20 mL) and the supernatant solutions were combined and evaporated. The residue was partitioned between EtOAc (30 mL) and 2.5% $NaHCO_3$ (30 mL). The EtOAc solution was washed with an equal volume of brine, dried, filtered and evaporated. The ester was dissolved in DCM (2 mL) and 0.5 mL of HCl/$Et_2O$ solution (1 M) was added. The resulting solution was stirred for 10 min, the $Et_2O$/DCM supernatant was decanted, the residue taken up in $Et_2O$, evaporated and dried in a vacuum oven to afford 0.118 g of I-13 containing about 12% of R-73.

Example 9

Phosphoric acid mono-{3-[4-bromo-3-(3-chloro-5-cyano-phenoxy)-2-fluoro-benzyl]-pyrazolo[3,4-c]pyridazin-1-ylmethyl}ester (I-18)

step 1—To a suspension of 10 (1.24 g, 2.54 mmol) and DCM (100 mL) was added thionyl chloride (2 mL). The resulting solution was stirred for 1 h then evaporated and resuspended in benzene and re-evaporated to afford 1.32 g of 3-[6-bromo-3-(1-chloromethyl-1H-pyrazolo[3,4-b]pyridin-3-ylmethyl)-2-fluoro-phenoxy]-5-chloro-benzonitrile (16) as a yellow foam which was used in the next step without additional purification.

step 2—To a mixture of 16 (1.28 g, 2.54 mmol), di-tert-butylphosphate (1.06 g, 5.08 mmol), in MeCN (70 mL) was added $Ag_2O$ (0.59 g, 2.54 mmol) and the resulting mixture was stirred for 1 d at RT. The resulting mixture was filtered through CELITE®, the filtrate was evaporated and the crude product purified by $SiO_2$ chromatography eluting with a MeOH/DCM gradient (0 to 1% MeOH) to afford 1.1 g of phosphoric acid 3-[4-bromo-3-(3-chloro-5-cyano-phenoxy)-2-fluoro-benzyl]-pyrazolo[3,4-b]pyridin-1-ylmethyl ester di-tert-butyl ester (18)

step 3—To a solution of 18 (0.179 g) in DCM (2 mL) was added TFA (1 mL) and the resulting solution stirred at RT for 1 min. The solvents were removed with a stream of $N_2$ while maintaining the solution at RT or below. Benzene (10 mL) was added to the residue and the benzene was removed in vacuo while maintaining the bath at RT or below. The residue was stirred in anhydrous MeCN and aqueous 1.00 N NaOH (0.53 mL) was added which produced a white solid. The suspension was stirred for 5 min then filtered, washed with MeCN and the solid dried in a vacuum desiccator and dried overnight under high vacuum to afford 0.129 g of I-18 as a white solid: nmr ($D_2O$) δ 4.32 (2H, s, $CH_2$), 5.95 (2H, d, $CH_2O$), 7.07-7.41 (6H, m, Ar), 8.01 (1H, d, Ar), 8.47 (1H, d, Ar).

Example 10

Heteropolymer HIV Reverse Transcriptase Assay

Inhibitor $IC_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM $MgCl_2$, 5 μM dTTP, 0.15 μCi [$^3$H] dTTP, 5 μg/ml poly (rA) pre annealed to 2.5 μg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 3×200 μl of 10% TCA and 2×200 μl 70% ethanol. Finally, the plates were dried and radioactivity counted in a Packard TopCounter after the addition of 25 μl scintillation fluid per well. $IC_{50}$'s were calculated by plotting % inhibition versus $\log_{10}$ inhibitor concentrations. Representative $IC_{50}$ data is depicted in TABLE 2.

TABLE 2

| Compound | IC$_{50}$ μM |
|---|---|
| I-3[1] | 0.0049 |
| I-5 | 0.0074 |

[1]sodium salt

Example 11

Determination of Pharmacokinetic Parameters in Rats

Intact male IGS Wistar Han Rats Crl:WI(GLx/BRL/Han) IGS BR (Hanover-Wistar) rats weighing 200-250 g were used. Groups of two rats were used for each dose level of an experimental compound. Animals were allowed normal access to chow and water throughout the experiment. The test substance was formulated as an aqueous suspension containing 5 mg Hypromellose 2910, USP (50 cps); 4 mg Polysorbate 80, NF; 9 mg Benzyl Alcohol, NF; q.s. with Sterile water for injection, USP 2 or 25 mg/kg of the R-73 and was administered orally by gavage. A blood sample (0.3 mL) was collected from the treated rats at, 0.083, 0.25, 0.5, 1, 2, 4, 6, and 8 h from a jugular cannula and at 24 h by cardiac puncture. Samples were collected in tubes containing potassium oxalate/NaF and stored on ice during sampling procedure. The samples were spun in a refrigerated centrifuge at −4° C. as soon as possible and the plasma samples were stored in a −80° C. freezer until analysis. Aliquots of plasma (0.05 mL) were mixed with 0.15 mL of acetonitrile containing 200 ng/mL of internal standard. A set of calibration standards was prepared by mixing 0.05-mL, aliquots of plasma from untreated rats with 0.15 mL, acetonitrile containing 200 ng/mL of internal standard. Each plasma sample and calibration standard was vortexed thoroughly and then centrifuged at 3500 rpm for 20 min to precipitate the protein. Supernatant (150 μL each) from centrifugation was transferred into a 96-well plate for LC/MS/MS analysis.

Sample Analysis—Prodrugs were analyzed using high-performance liquid chromatography with tandem mass-spectrometry (HPLC/MS/MS). A BDS C18 guard column was placed prior to an ACE C18 50×2.1 mm column (5 mm) that was used for separation. Electrospray Ionization (ESI) was used for the ionization process. The mobile phase A contained 5 mM ammonium acetate in water with 0.1% formic acid and mobile phase B contained 50:50 MeOH:Acetonitril with 0.1% Formic Acid. Elution was performed with the following gradient with a flow rate of 0.3 mL/min.:

| Time | % A | % B |
|---|---|---|
| 0 min | 100 | 0 |
| 0.5 min | 100 | 0 |
| 2.0 min | 0 | 100 |
| 3.1 min | 100 | 0 |
| 4.0 min | 100 | 0 |

Representative data for compounds of the present invention is tabulated in TABLE 3.

Example 12

Determination of Pharmacokinetic Parameters in Dogs

Intact female Marshall Farms Beagle dogs weighing 8-13 kg were used. Groups of two dogs were used for each dose level of an experimental compound. Animals were allowed normal access to chow and water throughout the experiment. The test substance was formulated as an aqueous suspension containing 5 mg Hypromellose 2910, USP (50 cps); 4 mg Polysorbate 80, NF; 9 mg Benzyl Alcohol, NF; q.s. with Sterile water for injection, USP 2 or 25 mg/kg of the R-73 and was administered orally by gavage. A blood sample (1.0 mL) was collected from the treated dogs at, 0.25, 0.5, 1, 2, 4, 6, 8, and 24 8 h from a jugular vein. Samples were collected in tubes containing potassium oxalate/NaF and stored on ice during sampling procedure. The samples were spun in a refrigerated centrifuge at −4° C. as soon as possible and the plasma samples were stored in a −80° C. freezer until analysis. Aliquots of plasma (0.05 mL) were mixed with 0.15 mL of acetonitrile containing 200 ng/mL of internal standard. A set of calibration standards was prepared by mixing 0.05-mL aliquots of plasma from untreated rats with 0.15 mL acetonitrile containing 200 ng/mL of internal standard. Each plasma sample and calibration standard was vortexed thoroughly and then centrifuged at 3500 rpm for 20 min to precipitate the protein. Supernatant (150 μL each) from centrifugation was transferred into a 96-well plate for LC/MS/MS analysis. Sample analysis was carried out as described in the previous example.

TABLE 3

| | Rat | | | Dog | | |
|---|---|---|---|---|---|---|
| Cpd. No. | Dose | AUC$_{0\to\infty}$ ng * h/mL | C$_{max}$ (ng/mL) | Dose | AUC$_{0\to\infty}$ ng * h/mL | C$_{max}$ (ng/mL) |
| R-73 | 2 | 992 | 85 | 2 | 64 | 13 |
| I-3 | 25 | 18700 | 1520 | 11.7 | 5930 | 958 |
| I-7 | 2 | 969 | 90 | 2 | 1950 | 299 |
| I-15 | 2 | 3710 | 319 | 2 | 2860 | 531 |
| I-9 | 2 | 1239 | 121 | 2 | 2360 | 469 |

Example 13

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Referential Example A

3-Aryloxyphenylacetic Acids

[4-Chloro-3-(3-chloro-5-cyano-phenoxy)-2-fluoro-phenyl]-acetic acid (R-1) and [4-Chloro-3-(3-chloro-5-cyano-phenoxy)-2-fluoro-phenyl]-acetyl chloride (R-2)

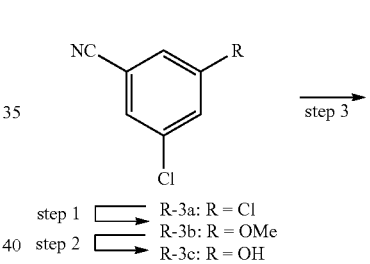

step 1: R-3a: R = Cl
step 2: R-3b: R = OMe
        R-3c: R = OH

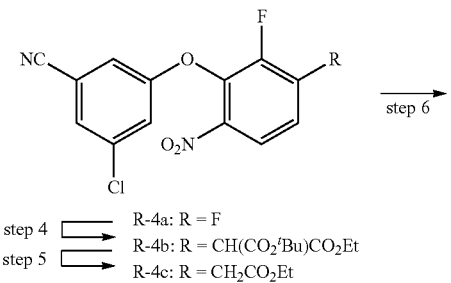

step 4: R-4a: R = F
step 5: R-4b: R = CH(CO$_2^t$Bu)CO$_2$Et
        R-4c: R = CH$_2$CO$_2$Et

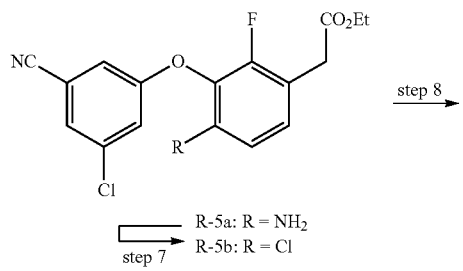

step 7: R-5a: R = NH$_2$
        R-5b: R = Cl

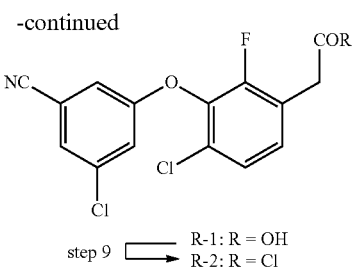

R-1: R = OH
R-2: R = Cl
step 9 step 1—A 100 ml round bottom flask was charged under a stream of nitrogen with 3,5-dichlorobenzonitrile (R-3a, 7.0 g, 40.69 mmol) and anhydrous DMF (75 mL). To the solution was added sodium methoxide (2.26 g, 44.76 mmol) and resulting solution was stirred further at RT for 24 h. When the reaction was complete, aqueous 10% HCl added dropwise to the reaction vessel. The crude mixture was extracted with EtOAc and sequentially washed with aqueous acid, water and brine. The EtOAc extracts were dried ($Na_2SO_4$), filtered and the solvent was removed in vacuo to afford a crude solid which was recrystallized from hexane/acetone to afford 5.9 g (86%) of R-3b.

step 2—A 250 mL flask was charged with R-3b (7.0 g, 41.766 mmol) and 2,4,6-collidine (100 mL). The mixture was heated to 170° C. and LiI (16.76 g, 125.298 mmol) was added and the reaction mixture was heated for 4 h. When R-3b was consumed the reaction was cooled to RT and quenched with 10% aqueous HCl. The resulting mixture was extracted with EtOAc and washed with water and brine. The EtOAc extract was dried over ($Na_2SO_4$) and filtered. The solvent was removed in vacuo to afford a yellow oil which was purified by silica gel chromatography eluting with EtOAc/hexane (10:90) to afford 6.0 g (94%) of R-3c.

step 3—A 250 mL round-bottom flask was charged with R-3c (6.0 g, 39.070 mmol) and anhydrous THF (100 mL) and the solution was cooled to 0° C. To the cooled solution was added sodium tert-butoxide (46.89 g, 4.51 mmol) and the resulting solution stirred for 1 h. 2,3,4-Trifluoro-nitro-benzene (6.92 g, 39.070 mmol) was added dropwise while maintaining the reaction at 0° C. until phenol was completely consumed. The mixture was quenched by addition of 10% aqueous HCl and the resulting mixture was stirred for an additional hour. The mixture was extracted with EtOAc and washed with water and brine. The EtOAc was dried ($Na_2SO_4$) and filtered. The solvent was removed in vacuo to yield a yellow oil which was purified by $SiO_2$ column chromatography eluting with hexane/EtOAc (92:8) to afford 10 g (82%) of R-4a.

step 4—To a solution of tert-butyl ethyl malonate (10.31 g, 54.80 mmol) and anhydrous NMP (200 mL) cooled to 0° C. and stirred under a nitrogen atmosphere. To this solution was added NaH 40% in mineral oil (1.84 g, 76.70 mmol). The mixture was allowed to stir at 0° C. for an additional 1 h. The bis-aryl ether R-4a (15.00 g, 49.80 mmol) was then added to the reaction vessel and stirred under nitrogen at RT until the reaction was complete. The mixture was quenched by addition of aqueous 10% HCl at RT. The mixture was extracted with EtOAc and washed with water and brine. The EtOAc was dried ($Na_2SO_4$) and filtered. The solvent was removed in vacuo to afford R-4b as a light yellow oil which was used in the next step without any further purification.

step 5—The diester R-4b (24.0 g, 50.117 mmol) was dissolved in dichloroethane (300 mL) and TFA (6.29 g, 55.13 mmol) and heated to 75° C. for 24 h. The mixture was cooled to RT and solvent and excess TFA were removed in vacuo. The crude oil was redissolved in DCM and cooled to 0° C. and aqueous $NaHCO_3$ was added. The mixture was extracted with DCM and washed with water and brine. The DCM was dried ($Na_2SO_4$), filtered and the solvent was removed in vacuo to afford a yellow oil. The crude oil was purified by $SiO_2$ chromatography eluting with hexane/EtOAc (90:10) to afford 15.0 g (80%) of R-4c.

step 6—A 250 mL round bottom flask was charged with R-4c (8.0, 21.12 mmol) and absolute EtOH. To the reaction vessel was added ammonium chloride (2.26 g, 42.244 mmol), water (30 mL) and iron (1.17 g, 21.12 mmol). The reaction was stirred and heated to 80° C. for 4 h. When R-4c was consumed, the heterogeneous mixture was filtered through a pad of CELITE® and the filter cake was washed with EtOAc. The aqueous filtrate was extracted with EtOAc and washed with water and brine. The combined EtOAc extracts were dried over ($Na_2SO_4$) and filtered. The solvent was removed in vacuo to afford a pale oil which was purified by $SiO_2$ chromatography eluting with hexane/EtOAc (85:15) to afford 6.0 g (87%) of R-5a.

step 7—A 100 mL round bottom flask was charged with anhydrous MeCN (15 mL) under a continuous stream of nitrogen. To this mixture was added Cu(II)$Cl_2$ (0.083 g, 0.624 mmol) and tert-butyl nitrite (0.064 g, 0.624 mmol). The mixture was heated to 70° C. 30 min. To this mixture was added R-5a (0.100 g, 0.624 mmol) in a single portion and stirring continued for an additional 2 h. Upon consumption of starting materials the mixture was cooled to RT and reaction mixture quenched with aqueous 10% HCl. The mixture was extracted with EtOAc and the combined extracts were washed with water and brine. The EtOAc extract was dried ($Na_2SO_4$) and filtered. The solvent was removed in vacuo to afford a light brown oil which was purified by $SiO_2$ chromatography eluting with hexane/EtOAc (96:4) to afford 0.080 g (76%) of R-5b.

step 8—A dried 100 mL round bottom flask purged with nitrogen and charged with R-5b (2.0 g; 5.43 mmol) and dissolved in THF (20 mL) and stirred under a stream of nitrogen. To the reaction vessel was added LiOH (0.46 g; 10.86 mmol) followed by 5 mL deionized water. The reaction was stirred for 1 h under a continuous stream of nitrogen. The homogeneous mixture was quenched at 0° C. with 10% aqueous HCl. The reaction mixture was stirred for an additional 15 minutes. The crude mixture was extracted with EtOAc and washed with water and brine. The organic extracts were dried ($Na_2SO_4$) and filtered. The solvent was removed in vacuo and the crude acid R-1 was used without any further purification.

step 9—A 100 mL round bottom was charged with R-1 (0.200 g, 0.520 mmol) and 5 mL of DCM and the solution was stirred under nitrogen at RT. To the solution was added thionyl chloride (0.061 g, 0.520 mmol) dropwise followed by a single drop of DMF. The reaction was stirred for 1 h at RT. Excess solvent and thionyl chloride were removed in vacuo to afford the carboxylic acid R-2 as a crude yellow oil which was used in the next reaction without any further purification.

General Procedure for the Preparation of Tert-Butyl Phenylacetates

To an ice-cold solution of the ethyl or methyl ester of a substituted phenyl acetic acid in THF is added an aqueous solution of LiOH.$H_2O$ (1.5 equivalents). The reaction mixture is stirred at RT and the progress of the hydrolysis is followed by tlc or hplc. When the reaction is complete 1M HCl and EtOAc are added and the organic phase is washed with brine, dried, filtered and evaporated to afford the corresponding carboxylic acid.

To a solution of the carboxylic acid in tert-butanol maintained under an inert atmosphere was added DMAP (0.3 equivalents and di-tert-butyl dicarbonate (Boc anhydride, 2 equivalents). The reaction is stirred at RT until gas evolution ceases and the reaction is complete. The solvent is removed in vacuo and the product purified by $SiO_2$ chromatography.

4-Chloro-3-(3,5-dicyano-phenoxy)-2-fluoro-phenyl]-acetic acid (R-7) and 4-chloro-3-(3,5-dicyano-phenoxy)-2-fluoro-phenyl]-acetyl chloride (R-8)

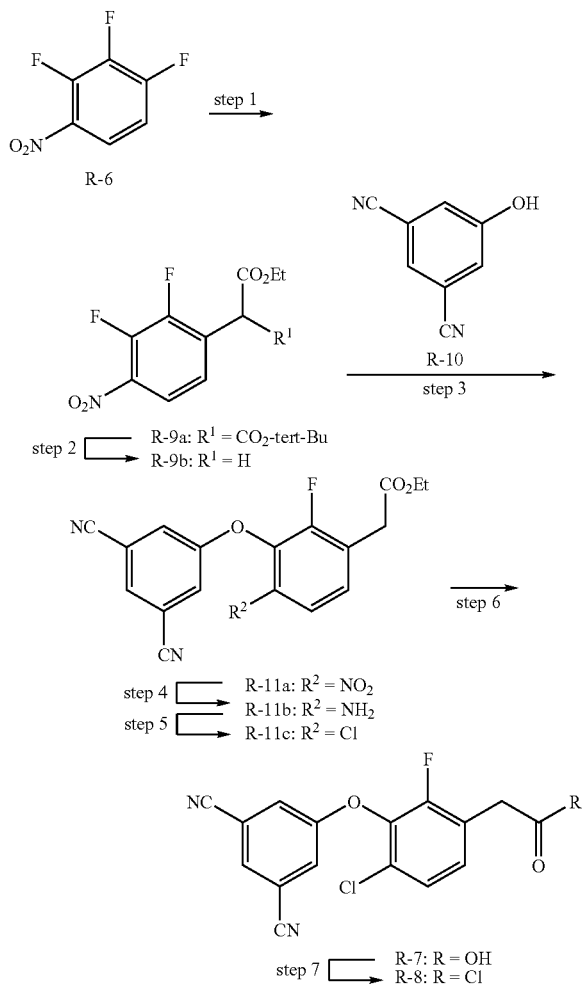

steps 1 & 2—ethyl 2,3-difluoro-4-nitrophenylacetate (R-9b)

To an ice-cold solution of tert-butyl ethylmalonate (Alfa Aesar) (31.2 g, 166 mmole) in NMP (300 mL) cooled to 0° C. under a nitrogen atmosphere was added NaH (60% oil dispersion, 13.1 g, 218 mmoles) while maintaining the temperature below 20° C. After addition complete, the solution was aged for 20 min. To this solution was added dropwise 2,3,4-trifluoronitrobenzene (R-6, Oakwood Products Inc.) (26.6 g, 163 mmole) in NMP (50 ml), while maintaining the temperature below 200 (highly exothermic). Upon completion of the addition the reaction was aged at RT for 2 h. The solution was added to an aqueous solution of $NH_4Cl$ (1.5 L), extracted with EtOAc (3×200 mL), washed 5 times with water (400 mL), dried ($MgSO_4$) and evaporated. The crude substituted malonic ester R-9a was used without further purification.

Ester R-9a was dissolved in DCM (400 mL) and TFA (100 mL) was added, this solution heated at 40° C. for 16 h. The reaction mixture was cooled to RT and the solvents evaporated. The crude product dissolved in EtOAc (400 mL), washed sequentially with aqueous $NaHCO_3$, water, and brine, dried ($MgSO_4$) and evaporated. The residual oil was purified by $SiO_2$ chromatography eluting with 5% EtOAc/hexanes to afford R-9b as a golden oil (11.9 g) (30%) which crystallizes upon sitting.

step 3—A solution of anhydrous THF (100 mL) and R-10 (10.00 g, 69.38 mmol) cooled to 0° C. was treated with sodium tert-butoxide (7.34 g, 76.32 mmol). The mixture was stirred for 30 min at 0° C. then R-9b (17.01, 69.38 mmol) was added and stirred for 3 h. The reaction was quenched with 10% aqueous HCl. The crude mixture was extracted with EtOAc and the combined extracts washed with water and brine. The organic phase was dried ($Na_2SO_4$) and filtered. The solvent was removed in vacuo to afford a crude oil which was purified by $SiO_2$ chromatography eluting with hexanes/EtOAc (90:10) to afford 20 g (78%) of R-11a.

Introduction of the chloro substituent (steps 4 & 5) were carried out as described in steps 6 & 7 of the preparation of R-1 (supra). Hydrolysis of the ester and formation of the acid chloride (steps 7 & 8) were carried out by the procedures described in steps 8 & 9 of the preparation of R-1 which afforded R-7 and R-8.

[4-Chloro-3-(3-cyano-5-difluoromethoxy-phenoxy)-2-fluoro-phenyl]-acetic acid ethyl ester (R12)

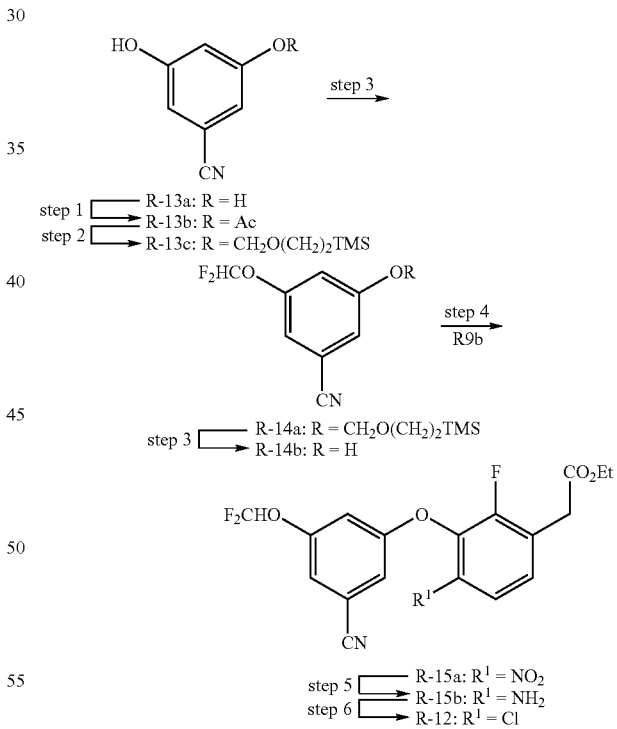

step 1—Acetic anhydride (30 mL, 4 equiv) was added to a solution of R-13a (10.36 g, 77 mmol) in anhydrous pyridine (60 mL) cooled to 0° C. and blanketed with nitrogen. The reaction was warmed to RT and stirred for 16 h. The volatile materials were removed in vacuo, and the remaining oil was dissolved in EtOAc, washed with water, 5% HCl solution, brine and dried ($MgSO_4$). The volatile materials were removed to afford 14.5 g (86%) of the diacetate. The diacetate (14 g, 64 mmol) was dissolved in a mixture of EtOH (100 mL)

and benzene (100 mL) and cooled to 0° C. A solution of KOH (3.6 g, 1 equiv) in EtOH was added dropwise. After 1 h, the solution was added to an ice-cold solution of saturated ammonium chloride, extracted with ether, and washed with brine. The Et$_2$O extracts were concentrated and purified by SiO$_2$ chromatography eluting with a hexane/EtOAc gradient (0% to 25% EtOAc) which afforded 10 g of R-13b (88%).

step 2—(2-Trimethylsilyl-ethoxy)-methyl-chloride (2.2 mL, 1.1 equiv) was added to a solution of the R-13b (2.0 g, 11.3 mmol) and DIPEA (2.4 mL, 1.2 equiv) in DCM (50 mL) cooled to 0° C. The solution was warmed to RT, stirred for 16 h, and poured into a saturated NaHCO$_3$ solution. The aqueous solution was extracted with DCM, and the combined organic extracts washed with water and brine and dried (MgSO$_4$). The solvents were removed in vacuo and the acetylated product was dissolved in a mixture of water (8 mL) and THF (32 mL). LiOH.H$_2$O (0.71 g, 1.5 equiv) was added. The mixture was stirred for 2 h, acidified to pH 5 and extracted with ether. The organic layer was dried (MgSO$_4$) and evaporated to provide 2.5 g (80%) of the R13-c.

step 3—F$_2$ClCCO$_2$Na (2.84 g, 2.3 equiv) was added to a solution of Cs$_2$CO$_3$ (3.69 g, 1.4 equiv), R-13c (2.26 g, 8.09 mmol), DMF (32 mL) and water (2 mL). The solution was heated to 100° C. for 2 h, cooled to RT, and poured into a sat'd. solution of NH$_4$Cl. The solution was extracted with a mixture of EtOAc and hexanes, and the organic layer was washed with brine and dried (MgSO$_4$). The crude product was purified by SiO$_2$ chromatography eluting with a EtOAc/hexane gradient (0% to 10%) which afforded 1.83 g (70%) of R-14a. The difluoromethyl ether R-14a was dissolved in MeOH (30 mL), and 5.6 mL of a 1.0 M solution of HCl was added. The solution was heated to 50° C. for 5 h, and stirred at RT for 16 h. The volatile materials were evaporated, and the aqueous residue was partitioned between DCM and water. The aqueous layer was extracted with DCM, and the combined extracts were washed with water and brine. The volatile materials were removed in vacuo to afford 780 mg (73%) of R-14b.

Condensation of R-14b and R-9b was carried out by the procedure described in step 3 of the preparation of R-7. Reduction of the nitro group (step 5), diazotization of the amine and displacement by chloride (step 6), hydrolysis of the ester and conversion of the acid to the acid chloride were carried out by the procedure described in steps 6-9 of the preparation of R-2.

[4-Chloro-3-(3-cyano-5-methoxy-1-phenoxy)-2-fluoro-phenyl]-acetic acid ethyl ester was prepared in similar fashion except in step 4,3-cyano-5-methoxy-phenol (CAS Reg. No. 124993-53-9) was used in place of R-14b.

[4-Chloro-3-(3-cyano-5-difluoromethyl-phenoxy)-2-fluoro-phenyl]-acetic acid ethyl ester (R-16a)

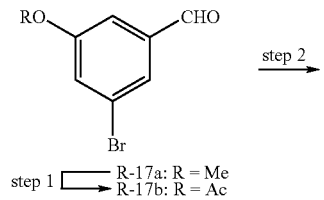

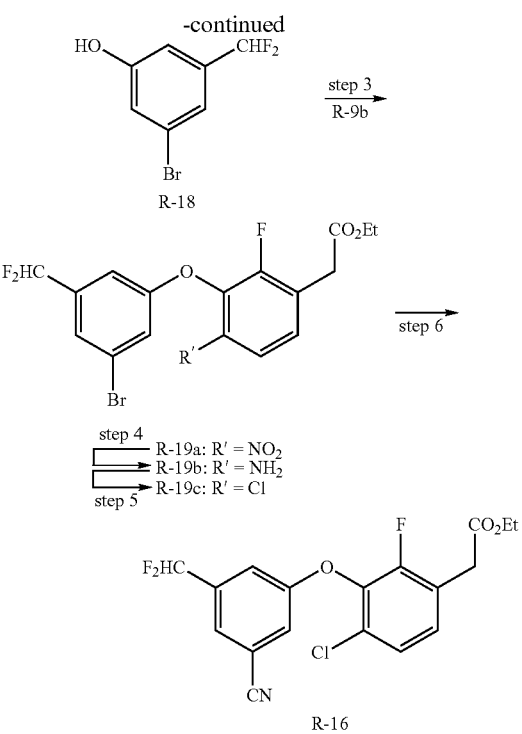

step 1—A solution of BBr$_3$ (29.1 mL of a 1.0 M solution in DCM, 29.1 mmol) was added slowly to a solution of R-17a (2.5 g, 11.62 mmol, CASRN 262450-65-7) in anhydrous DCM (25 mL) maintained under N$_2$ at −78° C. The orange solution was warmed to RT, stirred for 2 h, and poured onto ice. The mixture was extracted with DCM (100 mL), and the organic layer was washed with H$_2$O (50 mL) and brine (50 mL). The solvents were evaporated, and the remaining oil was purified by SiO$_2$ chromatography eluting with a EtOAc/hexanes gradient (0% to 20% EtOAc) to provide the desired phenol. To a solution of this phenol in pyridine (10 mL) under argon was slowly added acetic anhydride (0.6 mL, 6.33 mmol). After 2 h, the volatile materials were removed to provide 3-bromo-5-formyl-phenyl acetate (R-17b, 1.02 g, 40%).

step 2—DAST (1.02 mL, 7.69 mmol) was added to a solution of the 3-bromo-5-formyl-phenyl acetate (R-17b, 1.1 g, 4.52 mmol) in DCM (5 mL) under nitrogen contained in a NALGENE® bottle. EtOH (0.013 mL, 0.23 mmol) was added, and the mixture was stirred for 16 h. The reaction mixture was then added slowly to an aqueous solution of saturated NaHCO$_3$. After the bubbling ceased, DCM (50 mL) was added and the layers were separated. The organic layer was washed with brine (30 mL) and dried (MgSO$_4$). The solvent was removed to provide a yellow oil that was placed in a mixture of THF (15 mL) and H$_2$O (4 mL). LiOH monohydrate (474 mg, 11.3 mmol) was added, and the reaction mixture was stirred at RT for 2 h. The solution was then added dropwise to 5% aqueous HCl (50 mL), and the mixture was extracted with EtOAc (3×30 mL). The combined organic fractions were washed with brine (30 mL), and dried (MgSO$_4$). Evaporation of the volatile materials gave an oil that was purified by SiO$_2$ chromatography eluting with a EtOAc/hexanes gradient (0% to 25% EtOAc) to provide 800 mg (79%) of R-18.

Condensation of the phenol R-18 with R-9b (step 3) was carried out by the procedure described in step 3 of the preparation of R-7. Reduction of the nitro group (step 4), diazotization of the amine and displacement by chloride (step 5) to afford R-19c were carried out by the procedure described in steps 6 and 7 of the preparation of R-2.

step 6—A solution of R-19c (757 mg, 1.73 mmol), Pd[P(Ph)$_3$]$_4$(O) (300 mg, 0.26 mmol), and zinc cyanide (122 mg, 1.04 mmol) in DMF (8 mL) under nitrogen was heated to 80° C. for 4 h. The reaction mixture was cooled to RT and added to 2 M aqueous NH$_4$OH. The solution was extracted with 1:1 EtOAc/hexanes (3×30 mL), and the combined organic fractions were washed with H$_2$O (3×20 mL) and dried (MgSO$_4$). The solvent was evaporated, and the remaining oil was purified by SiO$_2$ chromatography eluting with an EtOAc/hexanes gradient (0% to 25% EtOAc) to provide 580 mg (87%) of R-16.

Hydrolysis of the ethyl ester and conversion to the acid chloride can be carried out as described in steps 8-9 of the preparation of R-2.

[3-(3-Bromo-5-cyano-phenoxy)-4-chloro-2-fluoro-phenyl]-acetic acid ethyl ester (R-20c)

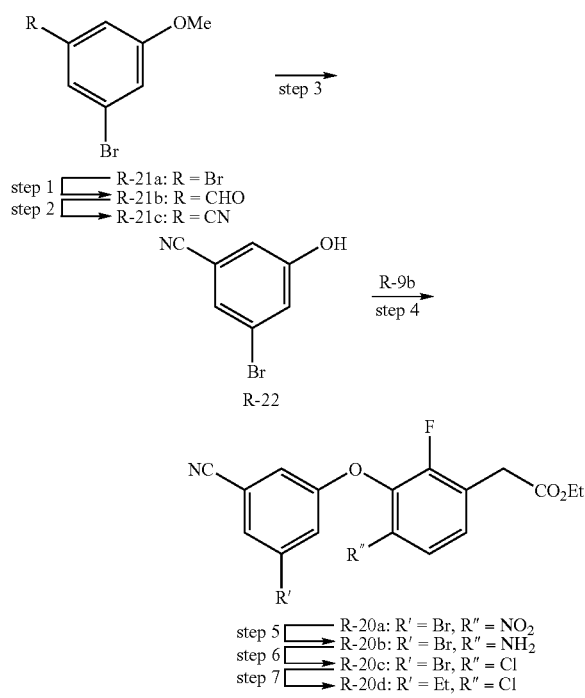

step 1—n-BuLi (2.6 mL of a 1.6 M solution, 1.1 equiv) was added slowly to a solution of the R-21a (1.0 g, 3.8 mmol, CAS Reg. No. 74137-36-3) in Et$_2$O (20 mL) cooled to −78° C. under an N$_2$ atmosphere. The solution was stirred for 45 min, and DMF was added via syringe. The solution was warmed slowly to RT, added to saturated ammonium chloride, and extracted with ether. The organic phase was washed with brine and dried (MgSO$_4$), filtered and evaporated to afford 0.80 g (98%) of R-21b.

step 2—A solution of the aldehyde R-21b (12.0 g, 56 mmol), hydroxylamine hydrochloride (19.4 g, 5 equiv), EtOH (100 mL) and pyridine (10 mL) was heated to 65° C. for 16 h. The mixture was cooled to RT, and partitioned between 50% EtOAc/hexanes and water. The organic layer was washed with brine and dried (MgSO$_4$). The volatile materials were evaporated to afford 12.4 g (97%) of the oxime. This material was dissolved in anhydrous dioxane (100 mL) and pyridine (26 mL, 6 equiv). The solution was cooled to 0° C., TFAA (15 mL, 2 equiv) was added, and the mixture was allowed to warm to RT. The solution was stirred for 2 d, and warmed to 60 C for 1 h. The mixture was cooled to RT, and added carefully to ice water. The mixture was extracted with DCM, and the combined organic layers were washed with water, 1 M HCl, and brine. The organic layer was dried (MgSO$_4$) and evaporated to afford 10.4 g (90%) of R-21c, step 3—Anhydrous collidine (100 mL) was added to a dry flask containing R-21c (10.4 g, 49 mmol) and LiI (19.6 g, 3 equiv). The solution was heated under nitrogen to 150° C. overnight, cooled to RT, and poured into an ice cold 1 M HCl solution. The mixture was extracted with a 1:1 EtOAc/hexanes solution, washed with water, and dried (MgSO$_4$). Concentration in vacuo afforded 8.7 g (89%) of R-22.

Condensation of the phenol R-22 with R-9b (step 4) was carried out by the procedure described in step 3 of the preparation of R-7. Reduction of the nitro group (step 5), diazotization of the amine and displacement by chloride (step 6) to afford R-20c were carried out by the procedure described in steps 6 and 7 of the preparation of R-2.

[4-Chloro-3-(3-cyano-5-ethyl-phenoxy)-2-fluoro-phenyl]-acetic Acid Ethyl Ester (R-20d) was prepared from by treating a THF solution of R-20c with, Pd(dppf)Cl$_2$, DIBAL-H (1M in toluene), diethylzinc utilizing the procedure described in the preparation of R-31 (infra).

[4-Bromo-3-(3-chloro-5-cyano-phenoxy)-2-fluoro-phenyl]-acetic acid ethyl ester (R-23a) and [4-Bromo-3-(3-chloro-5-cyano-phenoxy)-2-fluoro-phenyl]-acetic acid (R-23b)

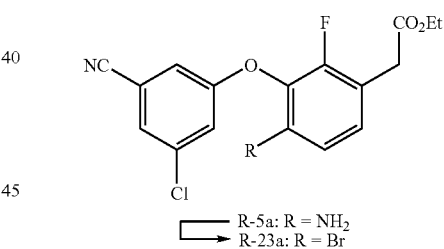

A 150 mL, three-neck round bottom flask was charged with MeCN (50 mL), CuBr$_2$ (2.8 g, 12.61 mmol) and t-butyl nitrite (1.4 g, 13.76 mmol), degassed and maintained under an Ar atmosphere and heated to 70° C. To the mixture was added dropwise a solution of R-5a (4.0 g, 11.47 mmol) dissolved MeCN (20 mL). The reaction mixture was stirred at 70° C. for 4 h and then cooled to 0° C. The reaction was quenched by addition of 10% HCl (30 mL) and extracted with EtOAc. The combined extracts were sequentially washed with 10% HCl and brine. The organic extract was dried (Na$_2$SO$_4$), filtered and the volatile solvents removed in vacuo to yield a black oil which was purified by SiO$_2$ chromatography eluting with hexanes/EtOAc (95:5) to afford 2.5 g (52.8%) of R-23a. Hydrolysis of the ethyl ester by the procedure described in step 8 of example 1 afforded the carboxylic acid R-23b.

[4-Bromo-3-(3,5-dicyano-phenoxy)-2-fluoro-phenyl]-acetic acid ethyl ester (R-24) was prepared from R-11b by reduction of the nitro as described in step 6 of the preparation of R-5a and diazotization of the amine and displacement with bromine as described for R-23.

[4-Bromo-3-(3-cyano-5-difluoromethyl-phenoxy)-2-fluoro-phenyl]-acetic acid ethyl ester (R-25)

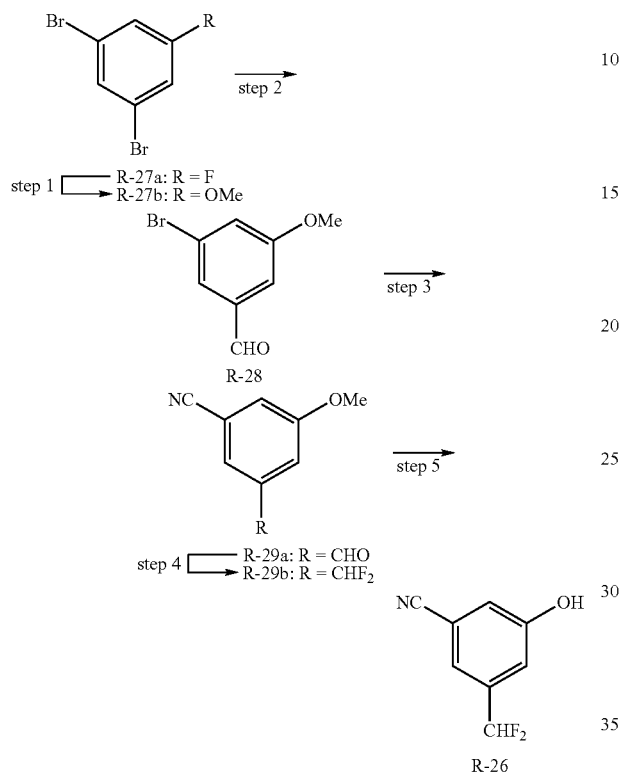

step 1—A solution of R-27a (CASRN 1435-51-4), MeONa (1 equivalent) and DMF were stirred overnight under an $N_2$ atmosphere at RT. The volatile solvents were removed in vacuo and the residue partitioned between $Et_2O$ and water. The organic phase was washed with 5% NaOH, water and brine, dried ($MgSO_4$), filtered and evaporated to afford R-27b.

step 2—To a solution of R-27b (60 g, 0.2256 mol) and anhydrous $Et_2O$ (1 L) cooled to $-78°$ C. and maintained under an Ar atmosphere was added dropwise over 30 min n-BuLi (100 mL, 0.2482 mol, 2.5M in hexane). The yellow solution was stirred at $-78°$ C. for 20 min. To the reaction mixture was added dropwise dry DMF (19 mL, 248.2 mmol) over 15 min and the reaction stirred at $-78°$ C. for 10 min before the cooling bath was removed and the reaction allowed to warm to $-30°$ C. over 30 min. The reaction vessel was placed in an ice-water bath and warmed to $-10°$ C. The mixture was slowly added to an ice cold saturated aqueous $NH_4Cl$ solution (400 mL). The organic layer was separated and the aqueous phase thrice extracted with $Et_2O$. The combined extracts were washed with water, dried ($MgSO_4$), filtered and evaporated to afford an oil which solidified on standing. The crude product was purified by $SiO_2$ chromatography eluting with a hexane/EtOAc gradient (3 to 5% EtOAc) to afford R-28.

step 3—Cyanation of R-28 to afford R-29a was carried out with $Zn(CN)_2$, $Pd(PPh_3)_4(0)$ and DMF as described in step 6 of the preparation of R-16 (supra)

step 4—DAST (21.04 mL, 519 mmol) was added to a solution of R-29a (15.1 g, 94 mmol) and DCM (100 mL) contained in a NALGENE® bottle under nitrogen. EtOH (0.013 mL, 0.23 mmol) was added, and the mixture was stirred for 16 h. The reaction mixture was then added slowly to an aqueous solution of saturated $NaHCO_3$. After the bubbling was ceased, DCM (50 mL) was added and the layers were separated. The organic layer was washed with brine (30 mL) and dried ($MgSO_4$). The solvent was removed and the crude product was purified by two flash $SiO_2$ chromatography's eluting with an EtOAc/hexanes gradient (0% to 10% EtOAc) to R-59b as a white solid.

step 5—The methyl ether R-59b was demethylated in a solution of 48% aqueous HBr and glacial HOAc heated to 120° C. until demethylation was complete. Removal of volatile and partitioning between water and DCM afforded R-26.

Condensation of R-26 and R-9b was carried out by the procedure described in step 3 of the preparation of R-7. Reduction of the nitro group was carried out as described in step 6 of the preparation of R-2. Diazotization and displacement of the diazole with bromine was carried out as described for R-23 to afford R-25.

[3-(3-Chloro-5-cyano-phenoxy)-2-fluoro-4-methyl-phenyl]-acetic acid ethyl ester (R-31)

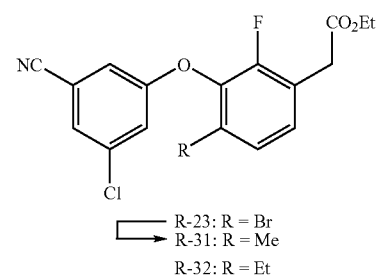

To a degassed ice-cold solution of THF (15 mL), Pd(dppf)$Cl_2$ (0.09 g, 0.121 mmol) was added DIBAL-H (0.012 mmol, 1M solution in toluene). The reaction mixture was allowed to warm to RT. A solution of R-23 (1.0 g, 2.42 mmol) was added followed by dimethyl zinc (1M in THF, 4.240 mmol). The reaction was heated to 65° C. for 4 μl, cooled to RT and quenched with aqueous $NH_4Cl$. The resulting mixture was extracted with EtOAc and washed sequentially with $NH_4Cl$ and brine. The EtOAc extract was dried ($Na_2SO_4$), filtered and the volatile solvent removed in vacuo to yield a dark brown oil that was purified by $SiO_2$ chromatography eluting with hexane/EtOAc (95:5) to afford 0.50 g (59%) of R-31.

[3-(3-Cyano-5-difluoromethyl-phenoxy)-2-fluoro-4-methyl-phenyl]-acetic acid ethyl ester (R-33) was prepared from R-25 using the procedure described above for R-31.

[3-(3,5-Dicyano-phenoxy)-2-fluoro-4-methyl-phenyl]-acetic acid ethyl ester (R-34) was prepared from R-24 using the procedure described above for R-31.

[3-(3-Chloro-5-cyano-phenoxy)-4-ethyl-2-fluoro-phenyl]-acetic acid ethyl ester (R-32) was prepared from R-23 using the procedure described for R-31 except diethylzinc was used in place of dimethylzinc.

[3-(3,5-Dicyano-phenoxy)-4-ethyl-2-fluoro-phenyl]-acetic acid ethyl ester (R-36) was prepared from R-24 using the procedure described for R-31 except diethylzinc was used in place of dimethylzinc.

[3-(3-cyano-5-difluoromethyl-phenoxy)-4-ethyl-2-fluoro-phenyl]-acetic acid ethyl ester (R-37) was prepared from R-25 using the procedure described for R-31 except diethylzinc was used in place of dimethylzinc.

[3-(3-Chloro-5-cyano-phenoxy)-4-cyclopropyl-2-fluoro-phenyl]-acetic acid ethyl ester (R-38)

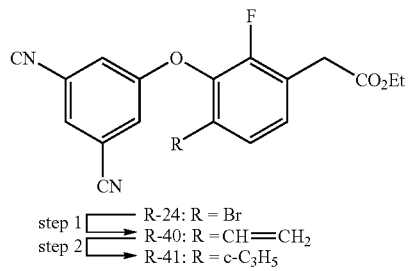

step 1 ⟶ R-24: R = Br
step 2 ⟶ R-40: R = CH=CH$_2$
        R-41: R = c-C$_3$H$_5$ step 1—To a solution of R-24 (0.80 g, 1.99 mmol), Pd(PPh$_3$)$_4$ (0.23 g, 0.10 equiv) and toluene (10 mL) was added tributylvinyltin (0.635 mL, 1.1 equiv) via syringe and the solution was refluxed for 5 h. The reaction was cooled to RT and poured into saturated aqueous NH$_4$Cl and extracted with EtOAc. The organic layer was washed with H$_2$O and brine, dried (MgSO$_4$) and evaporated. The resulting grayish brown solid was purified by SiO$_2$ chromatography eluting with a EtOAc/hexane gradient (0-25% EtOAc) to afford 0.60 g (85%) of R-40.

step 2—Diethyl ether (18 mL), H$_2$O (10 mL) and solid KOH (3 g) were combined in an Erlenmeyer flask and cooled to 0° C. Nitrosourea (1.17 g, 10 equiv) was added in portions and stirred for 1 h. The ether layer was decanted onto a bed of KOH and maintained at 0° C. In a separate flask, ester R-40 (0.4 g, 1.14 mmol) and Pd(OAc)2 (0.01 g, 0.05 equiv) were dissolved in Et$_2$O (10 mL) and DCM (5 mL) and cooled to 0° C. The decanted ethereal solution of diazomethane was added to this mixture and stirred for 3 h. The solution was filtered through CELITE® and SiO$_2$ and concentrated to afford 0.40 g (95%) of R-41.

[3-(3-Chloro-5-cyano-phenoxy)-4-cyclopropyl-2-fluoro-phenyl]-acetic acid ethyl ester (R-41a) was prepared analogously except in [4-bromo-3-(3-chloro-5-cyano-phenoxy)-2-fluoro-phenyl]-acetic acid ethyl ester (R-23a) was used in place of R-24.

[3-(3-Chloro-5-cyano-phenoxy)-2-fluoro-4-methoxy-phenyl]-acetic acid (R-42b)

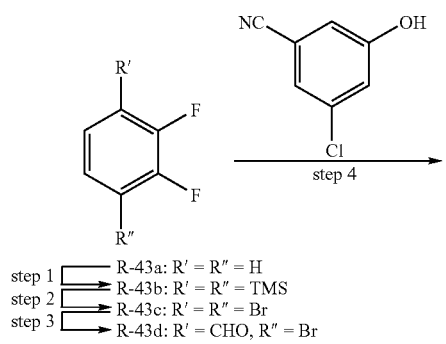

step 1 ⟶ R-43a: R' = R'' = H
step 2 ⟶ R-43b: R' = R'' = TMS
step 3 ⟶ R-43c: R' = R'' = Br
         R-43d: R' = CHO, R'' = Br

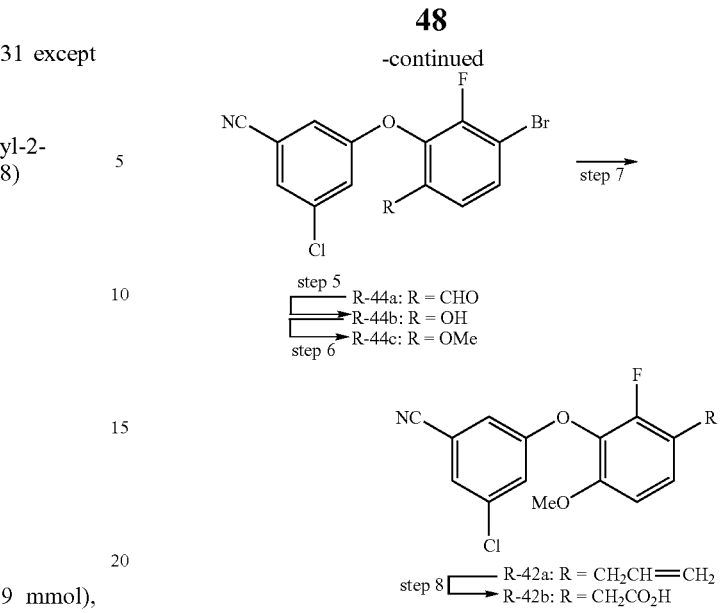

step 5 ⟶ R-44a: R = CHO
        R-44b: R = OH
step 6 ⟶ R-44c: R = OMe step 8 ⟶ R-42a: R = CH$_2$CH=CH$_2$
         R-42b: R = CH$_2$CO$_2$H step 1—To a solution of di-iso-propylamine (150 mL, 108.3 g, 1.07 mol) in THF (500 mL) cooled to −78° C. and maintained under a N$_2$ atmosphere was added over a 15 min period, n-BuLi (100 mL, 1.00 mol, 10M in hexanes). The resulting mixture was stirred for 30 min at −78° C. A mixture of R-43a (45 mL, 52.110 g, 0.457 mol) and chlorotrimethylsilane (130.0 mL, 111.28 g, 1.024 mol) was added at a rate which maintained the internal reaction temperature below −50° C. The solution was stirred at −78° C. for 1 h. The reaction was quenched at −78° C. by addition of 1M H$_2$SO$_4$, diluted with MTBE and the mixture was saturated with solid NaCl. The phases were separated and the aqueous phase was extracted with MTBE (300 mL). The combined organic extracts were dried (MgSO$_4$), filtered and the solvents evaporated to afford 118 g (100%) of R-43b as a white solid.

step 2—To neat Br$_2$ (76.9 ml, 1.50 mol) cooled to 0° C. in an ice bath was added portion wise solid R-43b (126.23 g, 0.500 mol) while maintaining the internal temperature between 20-45° C. (caution: exothermic!). The reaction mixture was stirred at 58° C. for 2 h. After 1 h of this period had elapsed additional bromine (45.48 g) was added and the addition funnel was rinse with cyclohexane (10 mL). The reaction mixture was cooled to 0° C. and slowly poured into ice-cold saturated NaHSO$_3$ solution. After the addition the resulting mixture was saturated with solid NaCl, extracted with MTBE (500 mL and 200 mL), dried (MgSO$_4$) and concentrated in vacuo to afford 191 g of R-43c. The reaction mixture was distilled at ca. 60 mbar which afforded 161.53 g of colorless liquid which boiled at 110° C. and contained about 11% of the monobromo derivative. The product was redistilled through a bubble ball column at ca. 50 mbar which afforded 141.3 (78.5%) of R-43c with a boiling point of 93-94° C. which was >99.6 pure.

step 3—Preparation of iso-PrMgCl.LiCl—A sample of LiCl (4.56 g, 107.6 mmol) was dried under high vacuum with a heat gun for 10 min. To the dry solid under a N$_2$ atmosphere at 23° C. was added iso-PrMgCl (53.8 mL, 107.6 mmol, 2M solution in THF) and the resulting mixture was stirred at 23° C. for 3 days.

To a solution of R-43c (1.29 mL, 10 mmol) in THF (5 mL) at −40° C. was added the iso-PrMgCl.LiCl solution (5.5 mL, 11 mmol, 2.0M in THF) at a rate that maintained the reaction temperature below −30° C. Stirring was continued at −35 to −30° C. for 1 h then warmed to −7° C. for an additional 1 h.

The reaction mixture was cooled to −30° C. and DMF (1.00 mL, 13 mmol) was added in one portion (temperature rose to −23° C.) and stirring continued for 3.5 h at −25 to +15° C. The reaction mixture was poured into 1M H₂SO₄ and ice and the resulting mixture was saturated with solid NaCl and twice extracted with MTBE. The combined extracts were dried (MgSO₄), filtered and concentrated in vacuo to afford 2.17 g (98%) of R-43d as a white solid.

step 4—To a solution of 3-chloro-5-hydroxy-benzonitrile (3.84 g), K₂CO₃ powder (4.2 g) and n-butyl nitrile was added R-43d (5.57 g). The reaction mixture was heated to reflux for 4.5 h when the reaction appeared complete by gc/ms. The reaction mixture was cooled and poured into water and then EtOAc was added. The resulting mixture was allowed to stand until the layers separated. Some crystals were present at the interface and along the walls of the upper layer which were filtered and washed with water and hexanes. The filtrate was evaporated in vacuo, the residue taken up in IPA and re-evaporated. The solid was triturated with hexane and filtered. The mother liquor was evaporated and the residue purified by SiO₂ chromatography eluting with hexane/EtOAc (80:20). The product was triturated with IPA, filtered and washed with hexanes and the product fractions combined to afford 1.45 g (83%) of R-44a.

step 5—Trifluoroacetic anhydride (8.88, 4.231 mmol) was added to a 100 mL, round bottom and stirred at 0° C. 30% Hydrogen peroxide (0.290, 8.46 mmol) was then added dropwise to the reaction vessel and stirred for 2 hours at zero to produce trifluoroperacetic acid (TFPA).

To a solution of R-44a (2.0, 5.64 mmol) in DCM (20 mL) stirred at 0° C. was added KH₂PO₄ (15.35 g, 112.82 mmol). To this suspension was added dropwise at 0° C. the TFPA. The reaction was stirred for 48 h. Upon consumption of starting material reaction mixture was cooled to 0° C., and diluted with brine, and quenched with aqueous 10% sodium bisulfite. The resulting mixture was extracted with DCM and washed with brine, dried (Na₂SO₄), filtered and the solvent removed in vacuo to yield a yellow solid which was purified by SiO₂ chromatography eluting with hexane/EtOAc (92:8) to afford 1.8 g (94%) of R-44b.

step 6—To a solution of R-44b (1.8 g, 5.26 mmol) in DMF (15 mL) was added Cs₂CO₃ (3.43, 10.52 mmol) and iodomethane (0.74 g, 5.26 mmol). The reaction mixture was stirred at 85° C. for 12 h. When R-44b was consumed, the reaction mixture was cooled to RT and the cured mixture extracted with EtOAc and the combined extracts washed with water and brine. The EtOAc was dried (Na₂SO₄), filtered and concentrated in vacuo to afford R-44c as a yellow oil which was used in the next step without additional purification.

step 7—A dry 100 mL, round bottom was purged with nitrogen and charged with R-44c (1.6 g, 4.50 mmol) and anhydrous THF (20 mL). The mixture was cooled to −20° C. and a solution of iso-PrMgCl.LiCl (5.40 ml, 5.40 mol, 2M in THF, see step 3) was added dropwise. The reaction was stirred for 2 h at −20° C. and a solution of CuCN LiCl (0.100 mL, 0.100 mol 1 M in THF) was added and stirred continued at −20 C. To this mixture was added allyl bromide (1.08 g, 9.0 mmol) and the mixture stirred for an additional two h. The reaction was quenched by addition of aqueous NH₄Cl. The mixture extracted with EtOAc and washed with water and brine. The extracts were dried (Na₂SO₄), filtered and the solvent was removed in vacuo to yield a yellow oil. The crude product was purified by SiO₂ chromatography eluting with hexane/EtOAc (95:5) to afford 1 g (70%) of R-42a.

step 8—To a solution of R-42a (0.100 g, 0.315 mmol), EtOAc (2 mL), MeCN (2 mL) and water (3 mL) was added NaIO₄ (0.437 g, 2.050 mmol) and RuCl₃ (0.001 g, 0.006 mmol). When R-42a was consumed, the crude mixture was filtered through a pad of CELITE®, washed with EtOAc and the combined EtOAc washes were washed with brine, dried (Na₂SO₄) filtered and evaporated in vacuo to afford 0.090 g (85%) of R-42b as a yellow solid. extracted with ethyl acetate, and washed with brine. The ethyl acetate was dried over sodium sulfate and filtered. Solvent was removed in vacuo to yield R-42b as a yellow solid (0.090 g, 85%).

[3-(3,5-Dicyano-phenoxy)-2-fluoro-4-methoxy-phenyl]-acetic acid (R-45) and [3-(3-cyano-5-difluoromethyl-phenoxy)-2-fluoro-4-methoxy-phenyl]-acetic acid (R-46) can be prepared similarly except R-10 and R-26 respectively are used in place of 3-chloro-5-hydroxy-benzonitrile.

Reference Example B

3-Chloro-5-[6-chloro-2-fluoro-3-(1H-indazol-3-ylmethyl)-phenoxy]-benzonitrile (R-52)

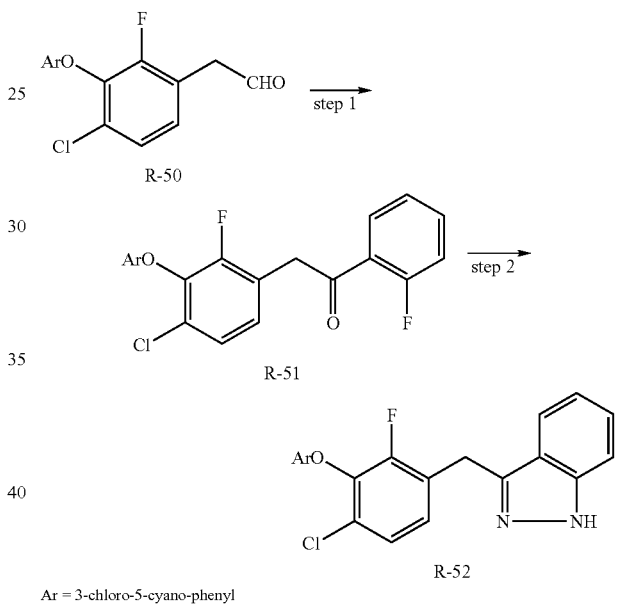

Ar = 3-chloro-5-cyano-phenyl

3-Chloro-5-[6-chloro-2-fluoro-3-(2-oxo-ethyl)-phenoxy]-benzonitrile (R-50) can be prepared by reduction of R-5b with diborane and the resulting alcohol can be re-oxidized to R-50 with CrO₃-pyridine.

step 1—i-PrMgCl (1.7 mL of a 2 M solution, 1.1 equiv) was added to a solution of 2-fluoro-bromobenzene (0.33 ml, 1 equiv) in THF (2 mL) cooled to 0° C. The solution was stirred at 0° C. for 1.25 h, then cooled to −78° C., and a solution of the R-50 (0.99 g, 3 mmol) in THF (2 mL) was added dropwise. The reaction mixture was warmed slowly to 0° C., and added to a cold aqueous solution of NH₄Cl. The solution was extracted with ether, and the combined organics were washed, dried, filtered and concentrated in vacuo. The crude residue was purified by SiO₂ chromatography eluting with an EtOAc/hexane gradient (0% to 25% EtOAc) to afford 0.57 g (44%) of the o-fluoro-phenyl adduct. A portion of the adduct (0.26 g, 0.62 mmol) was dissolved in DCM (3 mL), and Dess-Martin periodinane (0.32 g, 1.2 equiv) was added in one portion. After 4 h, the reaction was added to a saturated aqueous solution of Na₂S₂O₄. The mixture was extracted with DCM, washed, dried, and concentrated. The crude product was purified by SiO$_2$ chromatography eluting with an EtOAc/hexane gradient (0% to 20% EtOAc) to afford 0.23 g (87%) of R-51.

step 2—Hydrazine (0.24 mL, 10 equiv) was added to a solution of R-51 (0.32 g, 0.77 mmol) in a mixture of dioxane (3.6 mL) and EtOH (0.4 mL). After 2 h, the volatile materials were removed and purification of the residue by HPLC afforded 0.04 g (13%) of R-52.

3-[6-Bromo-2-fluoro-3-(1H-indazol-3-ylmethyl)-phenoxy]-5-difluoromethyl-benzonitrile (R-53) was prepared analogously from R-25 and 2-fluorobenzoic acid utilizing the Claisen condensation/hydrazine cyclization sequence.

3-[6-bromo-2-fluoro-3-(1H-pyrazolo[3,4-b]pyridin-3-ylmethyl)-phenoxy]-5-chloro-benzonitrile (R-54)

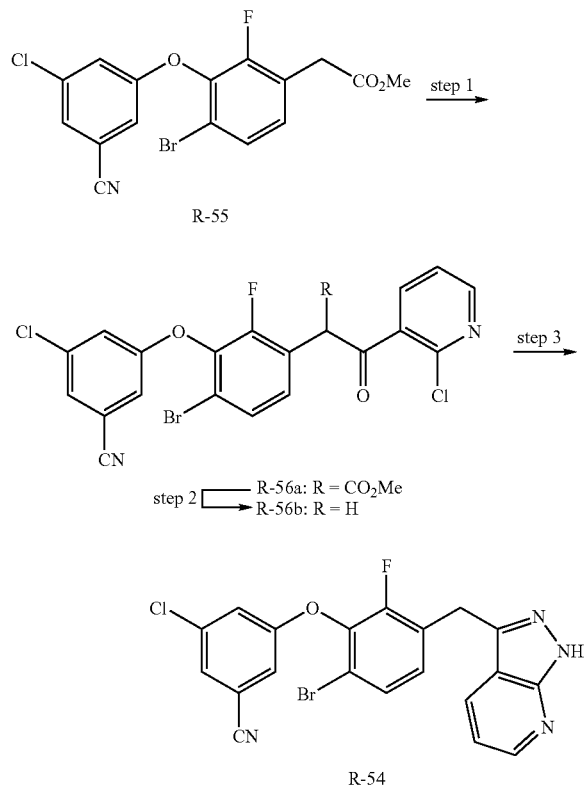

step 1—To a solution of 2-chloronicotinic acid (1.96 g, 12.5 mmol) in DMF (63 mL) was added CDI (2.02 g, 12.5 mmol) and the solution was heated to 50° C. After 2 h, the reaction mixture was cooled to −10° C., and to this was added sequentially a solution of R-55 (4.51 g, 11.3 mmol) in DMF (46 mL) and solid NaH (1.45 g, 36.2 mmol). (The methyl ester R-55 was prepared by the procedure described for R-23a except methyl t-butyl malonate was used in place of ethyl t-butyl malonate.) The reaction mixture was stirred at −10° C. for 15 min, then warmed to RT and stirred for 14 h. The reaction mixture was partitioned between NH$_4$Cl and EtOAc. The aqueous layer was extracted with EtOAc and the combined organic extracts were washed with 1N HCl, brine, dried (MgSO$_4$), filtered and concentrated in vacuo. The crude product was purified by column chromatography on SiO$_2$ eluting with an EtOAc/hexane gradient (25 to 30% EtOAc) to afford 3.25 g (53%) of R-56a.

step 2—A solution of R-56a (3.25 g, 6.04 mmol) in DMSO (35 mL) and H$_2$O (1.7 mL) was stirred in a preheated 150° C. oil bath for 30 min. The reaction mixture was partitioned between EtOAc and saturated aqueous NaHCO$_3$. The aqueous phase was extracted with EtOAc (3×50 mL) and the combined organic extracts were dried (MgSO$_4$), filtered and concentrated in vacuo to afford 2.45 g (85%) of R-56b as a yellow oil.

step 3—To a solution of R-56b (2.3 g, 4.8 mmol) in dioxane (41 mL) and EtOH (6 mL) was added hydrazine (1.50 mL, 10 equiv.) and the reaction mixture was heated to 100° C. After 2 h., the reaction mixture was cooled to RT and the solvent was removed. The residue was partitioned between 10% MeOH/DCM and saturated aqueous NaHCO$_3$. The aqueous layer was back-extracted with 10% MeOH/DCM and the combined organic extracts were dried (MgSO$_4$) filtered and concentrated in vacuo to afford a yellow solid that was triturated with 30% EtOAc/hexanes to afford 1.91 g (87%) of R-54 as a white solid.

3-Chloro-5-[6-chloro-2-fluoro-3-(1H-pyrazolo[3,4-b]pyridin-3-ylmethyl)-phenoxy]-benzonitrile (R-57) was prepared similarly from [4-chloro-3-(3-chloro-5-cyano-phenoxy)-2-fluoro-phenoxy]-acetic acid ethyl ester (R-5b).

5-[6-Bromo-2-fluoro-3-(1H-pyrazolo[3,4-b]pyridin-3-ylmethyl)-phenoxy]-isophthalonitrile (R-58) was prepared similarly from [4-bromo-3-(3,5-dicyano-phenoxy)-2-fluoro-phenyl]-acetic acid ethyl ester (R-24).

3-Chloro-5-[2-fluoro-6-methyl-3-(1H-pyrazolo[3,4-b]pyridin-3-ylmethyl)-phenoxy]-benzonitrile (R-59) was prepared similarly from [3-(3-chloro-5-cyano-phenoxy)-2-fluoro-4-methyl-phenyl]-acetic acid ethyl ester (R-31).

5-[6-Cyclopropyl-2-fluoro-3-(1H-pyrazolo[3,4-b]pyridin-3-ylmethyl)-phenoxy]-isophthalonitrile (R-60) was prepared similarly from [4-cyclopropyl-3-(3,5-dicyano-phenoxy)-2-fluoro-phenyl]-acetic acid ethyl ester (R-41).

3-Chloro-5-[6-ethyl-2-fluoro-3-(1H-pyrazolo[3,4-b]pyridin-3-ylmethyl)-phenoxy]-benzonitrile (R-61) was prepared similarly from [3-(3-chloro-5-cyano-phenoxy)-4-ethyl-2-fluoro-phenyl]-acetic acid ethyl ester (R-32).

3-Chloro-5-[6-cyclopropyl-2-fluoro-3-(1H-pyrazolo[3,4-b]pyridin-3-ylmethyl)-phenoxy]-benzonitrile (R-62) was prepared similarly from 3-(3-chloro-5-cyano-phenoxy)-4-cyclopropyl-2-fluoro-phenyl]-acetic acid ethyl ester (R-41).

3-[6-Chloro-2-fluoro-3-(1H-pyrazolo[3,4-b]pyridin-3-ylmethyl)-phenoxy]-5-difluoromethyl-benzonitrile (R-63) was prepared similarly from [4-chloro-3-(3-cyano-5-difluoromethyl-phenoxy)-2-fluoro-phenyl]-acetic acid ethyl ester (R-16).

3-[6-Bromo-2-fluoro-3-(1H-pyrazolo[3,4-b]pyridin-3-ylmethyl)-phenoxy]-5-difluoromethyl-benzonitrile (R-64) was prepared similarly from [4-bromo-3-(3-cyano-5-difluoromethyl-phenoxy)-2-fluoro-phenyl]-acetic acid ethyl ester (R-25).

3-Difluoromethyl-5-[2-fluoro-6-methyl-3-(1H-pyrazolo[3,4-b]pyridin-3-ylmethyl)-phenoxy]-benzonitrile (R-65) was prepared similarly from [3-(3-cyano-5-difluoromethyl-phenoxy)-2-fluoro-4-methyl-phenyl]-acetic acid ethyl ester (R-33).

3-[6-Ethyl-2-fluoro-3-(1H-pyrazolo[3,4-b]pyridin-3-ylmethyl)-phenoxy]-isophthalonitrile (R-66) was prepared similarly from [3-(3,5-dicyano-phenoxy)-4-ethyl-2-fluoro-phenyl]-acetic acid ethyl ester (R-36).

3-[6-Bromo-2-fluoro-3-(1H-pyrazolo[3,4-c]pyridin-3-ylmethyl)-phenoxy]-5-chloro-benzonitrile (R-67)

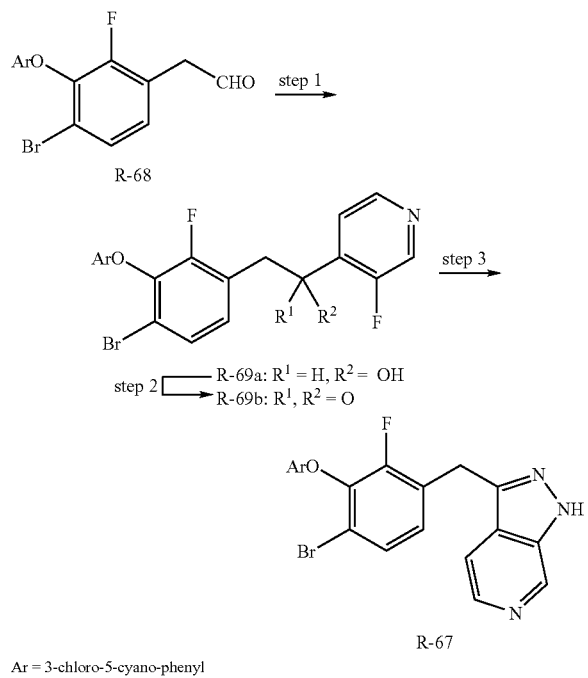

Ar = 3-chloro-5-cyano-phenyl

3-Chloro-5-[6-bromo-2-fluoro-3-(2-oxo-ethyl)-phenoxy]-benzonitrile (R-68) is prepared by reduction of R-23a with diborane and resulting alcohol is re-oxidized to R-68 with $CrO_3$-pyridine.

step 1—A THF solution of i-PrMgCl (1 equiv of a 2M solution) is added dropwise to a solution of 4-chloro-3-fluoro-pyridine (1 equivalent) in THF cooled to −40° C. and maintained under $N_2$. The solution is stirred for 30 min, and a solution of the R-68 (1 equiv) in THF is added dropwise. The reaction mixture is warmed to 0° C., is aged for 1 h, and is added dropwise to a pH 7 buffered aqueous solution. The aqueous mixture is extracted with EtOAc, the combined extracts are washed with brine, dried ($MgSO_4$) and concentrated in vacuo. The crude product is purified by $SiO_2$ chromatography eluting with an EtOAc/hexane gradient to afford 0.21 g (45%) of R-69a.

step 2—To a solution of the R-69a in DCM cooled to 0° C. is added the Dess-Martin periodinane (1.2 equiv). The mixture is stirred for 4 h, quenched with $NaHCO_3$ and the organic phase is separated and evaporated. The residue is purified by $SiO_2$ chromatography eluting with an EtOAc/hexane gradient to afford R-69b.

step 3—Hydrazine (0.288 mL, 5 equiv) was added to a solution of R-69b (0.85 g, 1.8 mmol) in dioxane (9 mL) and EtOH (0.5 mL). The solution was heated to 80° C. for 3 h. The solution was partitioned between EtOAc and water. Separation of the organic layer and evaporation of the residue afforded an oil that was purified by $SiO_2$ chromatography eluting with a MeOH/DCM gradient (0% to 5% MeOH) to afford 0.24 g (29%) of R-67.

5-[6-Bromo-2-fluoro-3-(1H-pyrazolo[3,4-c]pyridin-3-ylmethyl)-phenoxy]-isophthalonitrile (R-70) was prepared similarly starting from [4-bromo-3-(3,5-dicyano-phenoxy)-2-fluoro-phenyl]-acetic acid ethyl ester (R-24).

3-[6-Bromo-2-fluoro-3-(1H-pyrazolo[3,4-c]pyridin-3-ylmethyl)-phenoxy]-5-difluoromethyl-benzonitrile (R-71) was prepared similarly starting from [4-bromo-3-(3-cyano-5-difluoromethyl-phenoxy)-2-fluoro-phenyl]-acetic acid ethyl ester (R-25).

3-[6-Chloro-2-fluoro-3-(1H-pyrazolo[3,4-c]pyridin-3-ylmethyl)-phenoxy]-5-difluoromethyl-benzonitrile (R-72) was prepared similarly from [4-chloro-3-(3-cyano-5-difluoromethyl-phenoxy)-2-fluoro-phenyl]-acetic acid ethyl ester (R-16).

3-[6-Bromo-2-fluoro-3-(1H-pyrazolo[3,4-c]pyridazin-3-ylmethyl)-phenoxy]-5-chloro-benzonitrile (R-73)

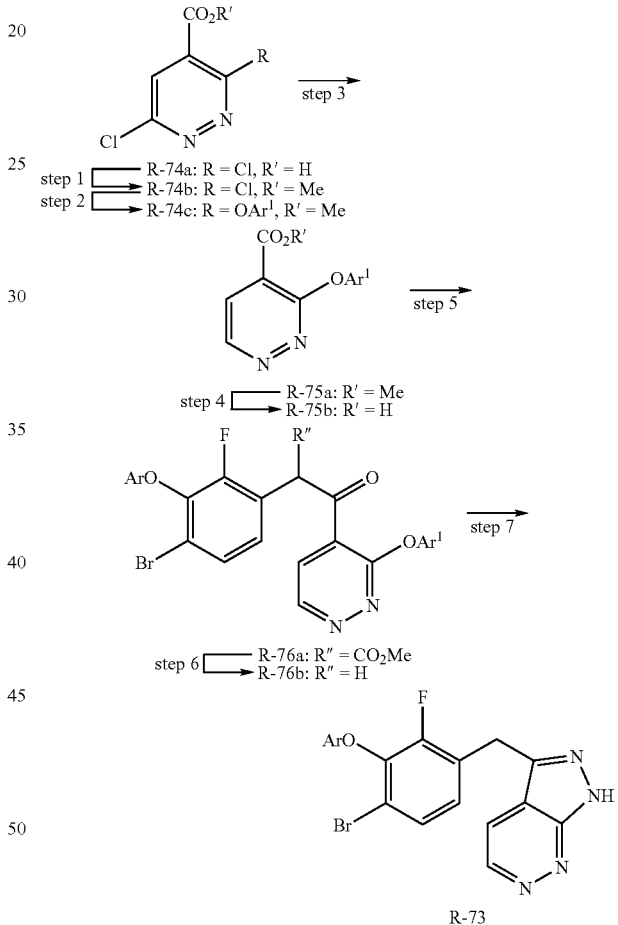

Ar = 3-chloro-5-cyano-phenyl
$Ar^1$ = 2,4-difluoro-phenyl step 1—To a solution of 3,6-dichloro-4-carboxy-pyridazine (R-74a, 7.5 g, 38.9 mmol, Aldrich) in DCM (30 mL) and MeOH (10 mL) cooled to 0° C. was added a solution of (trimethylsilyl)diazomethane (2.0 M in hexane), slowly via pipette, until a persistent yellow color is observed. After addition was complete, the solvents were removed in vacuo. The crude product was purified by $SiO_2$ chromatography eluting with an EtOAc/hexane gradient (10 to 25% EtOAc) to afford 3.89 g (86%) of R-74b as a brown oil that solidifies on standing.

step 2—Sodium hydride (1.53 g, 38.27 mmol) was suspended in dry THF (70 mL) under a $N_2$ atmosphere, cooled to 0° C. and 2,4-difluorophenol (3.31 mL, 34.94 mmol) was added dropwise, via syringe. After the addition was complete the mixture was stirred for 15 min, then the cooling bath was removed for 30 min and finally the solution was again cooled to 0° C. A solution of R-74b (6.89 g, 33.28 mmol) in dry THF (20 mL) was added through a cannula. The resulting mixture was stirred at RT overnight and then heated to 50° C. for 3 h. The reaction was cooled to RT and saturated $NH_4Cl$ (40 mL) was added followed by water (60 mL). The mixture was thrice extracted with EtOAc, dried ($MgSO_4$), filtered and evaporated. The crude product was purified by $SiO_2$ chromatography eluting with an EtOAc/hexane gradient (10 to 20% EtOAc) to afford 8.15 g (82%) of R-74c as a light yellow oil.

step 3—To a solution of R-74c (8.15 g, 127.11 mmol) in MeOH (40 mL) was added ammonium formate (8.55 g, 1.1 eq) followed by 10% Pd—C (500 mg). The mixture was heated to 50° C. for 20 min and then to 60° C. for 35 min. The mixture was cooled to RT and filtered through a 2 cm plug of CELITE® which was rinsed well with MeOH. The volatile solvents were evaporated and the residual material partitioned between DCM (80 mL) and $H_2O$. The DCM layer was separated and the aqueous layer extracted twice with DCM and water (80 mL). The combined extracts were dried ($MgSO_4$), filtered and evaporated. The crude product was purified by $SiO_2$ chromatography eluting with an EtOAc/hexane gradient (10 to 50% EtOAc) to afford 5.5 g (76%) of R-75a as a semi-viscous yellow oil.

step 4—To a solution of R-75a (5 g, 18.78 mmol) in THF (40 mL) and MeOH (10 mL) was added an aqueous solution of LiOH (21.6 mL, 1 M solution). The mixture was stirred for 15 min when the reaction was complete as determined by TLC analysis. The mixture was concentrated and the residue was diluted with $H_2O$ (25 mL) and THF (20 mL) and then adjusted to pH 2-3 with 10% HCl. The resulting solid was collected by filtration, washed with water (50 mL) and EtOAc (30 mL) to obtain 4.08 g (86%) of R-75b as a white powder.

step 5—To a solution of R-75b (605 mg, 2.4 mmol) in DMF (10 mL) was added CDI (410 mg, 2.5 mmol). The mixture was heated to 50° C. under an Ar atmosphere for 1.5 h. The solution was cooled to −10° C. and a solution of R-55 (1 g, 2.5 mmol) in DMF (5 mL) was added via syringe. While stirring vigorously, NaH (336 mg, 8.4 mmol) was added in 3 portions over 20 min. The orange solution was stirred for another 10 min and then the cooling bath was removed. The mixture was stirred for 1 h at RT. The reaction mixture was diluted with saturated $NH_4Cl$ solution (20 mL), water (30 mL) and EtOAc (50 mL) and agitated. The EtOAc phase was washed brine (50 mL) and the brine solution was extracted with EtOAc (2×30 mL). The combined extracts were dried ($MgSO_4$), filtered and evaporated. The crude product was purified by $SiO_2$ chromatography eluting with an EtOAc/hexane gradient (40 to 100% EtOAc) to afford 685 mg (45%) of R-76a as a orange foam.

step 6—To a solution of R-76a (670 mg, 1.06 mmol) in DMSO (8 mL) was added water (0.4 mL) and brine (10 drops). The mixture was heated to 145° C. (oil bath temperature) under Ar atmosphere for 10 min. The solution was cooled to RT and water (60 mL), EtOAc (30 mL) and $Et_2O$ (30 mL) were added. The mixture was agitated and NaCl (2 gm) was added. The mixture was again agitated and the organic phase was collected, washed with brine solution (50%) and the brine solution back-extracted with EtOAc/$Et_2O$ (1:1, 2×50 mL). The combined organic phases were dried ($MgSO_4$), filtered and evaporated. The crude product was purified by preparative TLC developing with 40% EtOAc/hexanes to afford 380 mg (62%) of R-76b as a light yellow foam.

step 7—To a solution of R-76b (100 mg, 0.17 mmol) in MeOH (2 mL) was added tert-butyl carbazate (45 mg, 2 eq) followed by glacial HOAc (0.03 mL). The mixture was heated at 60° C. for 5 h and then stirred at RT overnight. The mixture was partitioned between DCM (20 mL) and 5% $NaHCO_3$ (20 mL). The aqueous phase was back-extracted with DCM (2×20 mL) and the combined organic extracts dried ($MgSO_4$), filtered and evaporated. This residue was dissolved in THF (4 mL) in a microwave vial, DBU (0.04 mL, 1.5 equivalents) was added the resulting solution was heated for 10-12 min at 150° C. in microwave. The mixture was partitioned among EtOAc (40 mL), water (30 mL) and saturated aqueous $NH_4Cl$ (5 mL). The organic phase was separated and the aqueous phase was back-extracted with EtOAc (2×30 mL). The combined extracts were dried ($MgSO_4$), filtered and evaporated. The crude product was purified by preparative TLC developing with 6% MeOH/DCM to provide 45 mg (58%) of R-73 the product as an off-white powder.

5-[6-Bromo-2-fluoro-3-(1H-pyrazolo[3,4-c]pyridazin-3-ylmethyl)-phenoxy]-isophthalonitrile; trifluoroacetate salt (R-77) was prepared analogously except in step 5, R-55 was replaced by R-24.

5-[6-Ethyl-2-fluoro-3-(1H-pyrazolo[3,4-c]pyridazin-3-ylmethyl)-phenoxy]-isophthalonitrile (R-78) was prepared analogously except in step 5, R-55 was replaced by R-36.

3-Chloro-5-[6-ethyl-2-fluoro-3-(1H-pyrazolo[3,4-c]pyridazin-3-ylmethyl)-phenoxy]-benzonitrile (R-79) was prepared analogously except in step 5, R-55 was replaced by R-32.

3-Chloro-5-[6-cyclopropyl-2-fluoro-3-(1H-pyrazolo[3,4-c]pyridazin-3-ylmethyl)-phenoxy]-benzonitrile (R-80) was prepared analogously except in step 5, R-55 was replaced by R-38.

5-[6-Cyclopropyl-2-fluoro-3-(1H-pyrazolo[3,4-c]pyridazin-3-ylmethyl)-phenoxy]-isophthalonitrile (R-81) was prepared analogously except in step 5, R-55 was replaced by R-41.

3-[6-Chloro-2-fluoro-3-(1H-pyrazolo[3,4-c]pyridazin-3-ylmethyl)-phenoxy]-5-chloro-benzonitrile (R-73a) is prepared analogously except in step 5, R-55 is replaced by R-5b.

5-[6-Chloro-2-fluoro-3-(1H-pyrazolo[3,4-c]pyridazin-3-ylmethyl)-phenoxy]-isophthalonitrile; trifluoroacetate salt (R-73b) is prepared analogously except in step 5, R-55 is replaced by R-11c.

3-Chloro-5-[6-difluoromethyl-2-fluoro-3-(1H-pyrazolo[3,4-c]pyridazin-3-ylmethyl)-phenoxy]-benzonitrile (R-82)

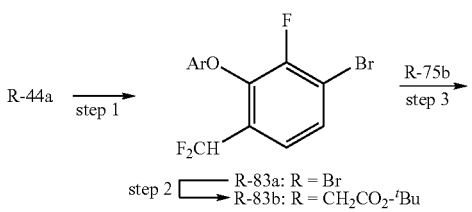

-continued

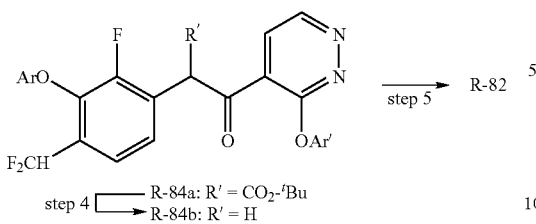

Ar = 3-chloro-5-cyano-phenyl; Ar' = 2,4-fluoro-phenyl step 1—To a solution of R-44a (3.2 g, 9.04 mmol) in DCM (12 mL) was added sequentially DAST (3.2 g, 2.2 eq) and EtOH (0.02 g, 0.05 eq) and the reaction mixture was stirred for 16 h. The reaction mixture was partitioned between aqueous NaHCO$_3$ and DCM. The organic layer was washed sequentially with water and brine, dried (Na$_2$SO$_4$), filtered and evaporated to afford 1.9 g (56%) of R-83a.

step 2—To a solution of R-83a (1.9 g, 5.045 mmol) and Pd(0)[P(tert-Bu)$_3$]$_2$ (0.39 g, 0.15 eq) in dioxane (30 mL) at RT was added 2-tert-butoxy-2-oxoethylzinc chloride (25 mL; 0.5M solution in ether) and the resulting solution was stirred at RT for 6 h. The reaction was partitioned between aqueous HCl and EtOAc. The organic layer was washed sequentially with water and brine, dried (Na$_2$SO$_4$), filtered and evaporated. The crude product was purified by SiO$_2$ chromatography eluting with an EtOAc/hexane gradient (2-12% EtOAc) to afford 0.65 g (30%) of R-83b.

step 3—To a solution of R-75b (0.088 g, 1.1 eq) and DMF (1 mL) was added CDI (0.06 g, 1.15 eq) and the solution was heated to 50° C. for 1 h. The reaction mixture was cooled to −25° C. and a solution of R-83b (0.13 g, 0.316 mmol) and DMF (1 mL) and NaH (0.04 g, 3.2 eq) were added. The reaction mixture was slowly warmed to RT and stirred for 6 h. The reaction mixture was partitioned between sat'd aqueous NaHCO$_3$ and EtOAc/hexanes (1:1). The organic layer was washed sequentially with H$_2$O and brine, dried (Na$_2$SO$_4$), filtered and evaporated to afford 0.200 g (98%) of R-84a.

step 4—A solution of R-84a (0.2 g, 0.31 mmol) and p-TsOH (0.015 g, 0.25 eq) in toluene (2.5 mL) was heated at 130° C. for 2 h. The reaction was cooled, and poured into sodium bicarbonate and extracted with EtOAc. The organic layer was washed sequentially with water and brine, dried (Na$_2$SO$_4$), filtered and evaporated. The crude product was purified by SiO$_2$ chromatography eluting with an EtOAc/hexane gradient (15-50% EtOAc) to afford 0.15 g (89%) of R-84b.

step 5—A solution of R-84b (0.15 g, 0.274 mmol), p-TsOH (0.10 g, 2 eq) and hydrazine (0.03 mL, 2 eq) in IPA (2 mL) was heated to 80° C. for 16 h. The reaction was cooled to 0° C. and H$_2$O (2.6 mL) was added. The pH of the resulting solution was adjusted to ca. 9 with 20% Na$_2$CO$_3$, then further diluted with H$_2$O (5 mL) and warmed up to RT for 1 h. The cloudy mixture was poured into EtOAc and the organic layer washed sequentially with water and brine, dried (Na$_2$SO$_4$), filtered and evaporated. The crude product was purified by SiO$_2$ chromatography eluting with a MeOH/DCM gradient (2.5-10% MeOH). The recovered material was triturated with EtOAc/hexanes to afford 0.040 g (34%) of R-82.

3-Chloro-5-[2-fluoro-6-methanesulfonyl-3-(1H-pyrazolo[3,4-c]pyridazin-3-ylmethyl)-phenoxy]-benzonitrile (R-85)

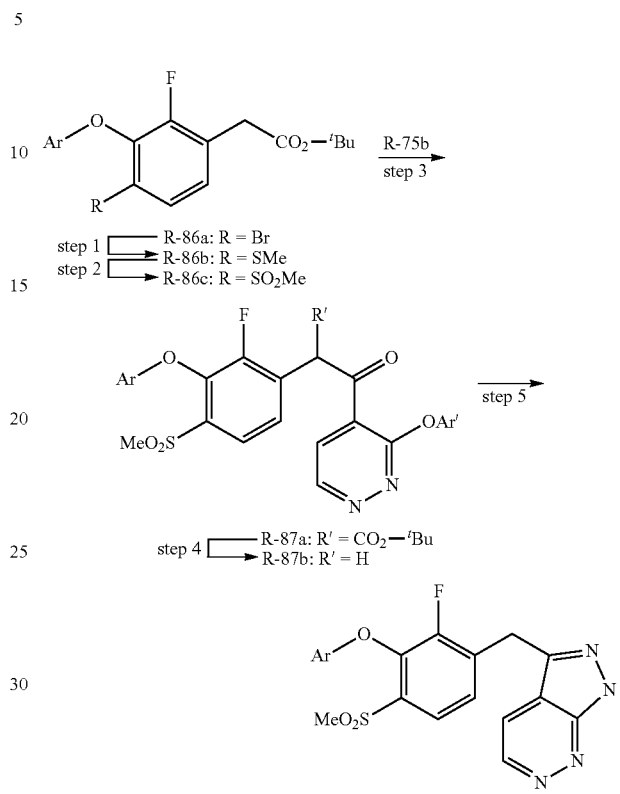

Ar = 3-chloro-5-cyano-phenyl; Ar$^1$-2,4-difluoro-phenyl step 1—To a solution of R-86a (4.03 g, 9.15 mmol) in m-xylene (60 mL) was added K$_2$CO$_3$ (846 mg, 6.12 mmol), Pd$_2$(dba)$_3$ (840 mg, 0.92 mmol), Xantphos (600 mg, 1.04 mmol, CASRN 161265-03-8) and NaSMe (810 mg, 11.56 mmol). The mixture was degassed and then heated to 135° C., under an argon balloon for 20 h. The reaction was cooled to RT and brine (80 mL) was added. The mixture was extracted with EtOAc (80 mL). The aqueous phase was back-extracted with EtOAc (2×70 mL) and dried (MgSO$_4$), filtered and concentrated in vacuo. The crude product was purified by SiO$_2$ chromatography eluting with an EtOAc/hexane gradient (5-20% EtOAc) to afford 2.3 of R-86b as a yellow oil.

step 2—To a solution of R-86b (2.4 g, 5.88 mmol) in MeOH (60 mL) and THF (8 mL) cooled to 0° C. (ice bath) was added dropwise a solution of OXONE® (7.35 g, 11.96 mmol) dissolved in water (22 mL). After the addition was complete the mixture was stirred for 15 min and then the cooling bath was removed. The resulting mixture was stirred overnight and then heated to 50° C. for 4 h. The reaction was cooled to RT and an aqueous solution of sat'd. NaHCO$_3$ was added dropwise until no further frothing observed. Water (20 mL) was added and the mixture was extracted with EtOAc (40 mL). The extracts were washed with brine (40 mL) and the brine was back-extracted with EtOAc (2×30 mL). The combined the EtOAc extracts were dried (MgSO$_4$), filtered and concentrated in vacuo to afford 2.5 g of R-86c as a light white-yellow solid.

step 3—To a solution of R-75b (274 mg, 1.1 mmol) in dry DMF (8 mL) was added CDI (188 mg, 1.2 mmol). The mixture was heated to 50° C. for 2 h then cooled to −10° C. A solution of R-86c (500 mg, 1.14 mmol) in DMF (5 mL) was added via syringe. To the cooled mixture was added NaH (152 mg, 3.81 mmol, 60% in mineral oil) over 20 min in three equal portions. After the addition was complete the mixture was stirred for 15 min and then the cooling bath was removed and stirring continued for 1 h. To the solution was carefully added sat'd aqueous $NH_4Cl$ (5 mL), followed by water (30 mL) and EtOAc (40 mL). The mixture was agitated and the EtOAc phase separated. The aqueous phase was back-extracted with EtOAc (2×30 mL). The combined extracts were dried ($MgSO_4$), filtered and evaporated. The crude product was purified by $SiO_2$ chromatography eluting with an EtOAc/hexane gradient (50 to 100% EtOAc) to afford 0.256 g of R-87a as a yellow foamy solid.

step 4—To a solution of R-87a (256 mg, 0.38 mmol) in anisole (5 mL) was added powdered boric anhydride (133 mg). The mixture was heated to 140° C. for 1 h and then cooled to RT. The mixture was concentrated in vacuo. The residue was cooled (ice bath) and partitioned between water (25 mL) and EtOAc (25 mL). The mixture was stirred at RT for 1 h then agitated. The EtOAc phase was washed with brine (25 mL) and the aqueous solution back-extracted with EtOAc (2×20 mL). The combined organic extracts were dried ($MgSO_4$), filtered, and concentrated to afford 0.215 g of R-87b as a light orange-yellow solid.

step 5—To a solution of R-87b (215 mg, 0.38 mmol) in IPA (2 mL) was added p-TsOH (144 mg) and hydrazine hydrate (0.04 mL, 85%). The mixture was heated to 80° C. under a $N_2$ atmosphere for 18 h. The reaction mixture was cooled to RT and water (3.5 mL), 20% aqueous $Na_2CO_3$ (0.5 mL) then additional water (1.5 mL) were added sequentially. The mixture was stirred for 5 min and then allowed to stand for 1.5 h. The resulting precipitate (65 mg) was collected by filtration. A second crop (130 mg) was recovered from the filtrate. These semi-pure crops were combined and adsorbed on a $SiO_2$ preparative TLC plate and developed with EtOAc to afford 0.055 g of R-85 as a light white-orange solid.

3-[6-Chloro-2-fluoro-3-(1H-pyrazolo[3,4-c]pyridazin-3-ylmethyl)-phenoxy]-5-difluoromethyl-benzonitrile (R-90)

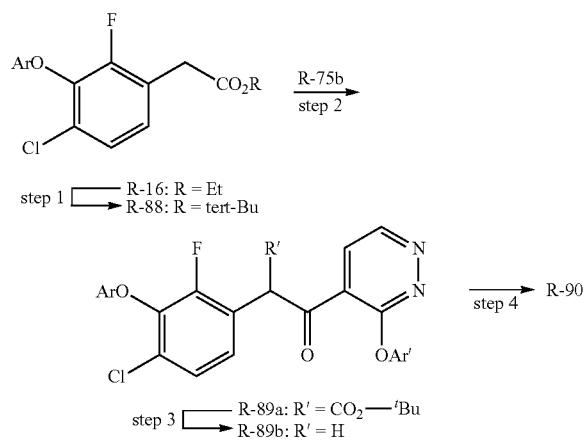

Ar = 3-difluoromethyl-5-cyano-phenyl; Ar' = 2,4-fluoro-phenyl step 1—R-16 was hydrolyzed to the corresponding carboxylic acid with LiOH in aqueous THF by stirring at RT for 3 h. Routine workup afforded the acid which was converted to the tert-butyl ester by stirring a tert-BuOH solution of the acid, Boc-anhydride and DMAP for 2 h. The crude product was purified by $SiO_2$ chromatography eluting with 5% EtOAc/hexane to afford R-88.

step 2—To a solution of R-75b (0.485 g, 1.92 mmol) and DMF (9 mL) in a flame-dried flask was added CDI (0.326 g, 2.01 mmol) and the solution was warmed to 50° C. for 65 min then cooled to 0° C. A solution of R-88 (0.720 g, 1.75 mmol) in a small amount of DMF was added followed by NaH (0.189 g 4.72 mmol, 50% mineral oil dispersion). The reaction was stirred for 1 h then added to cold sat'd. aqueous $NH_4Cl$. The solid precipitate was collected, washed with water and dried in vacuo to afford 0.978 g of R-89a as a brown solid.

step 3—To a solution of R-89a (0.978 g, 1.51 mmol) in anisole (7.5 mL) was added boric anhydride (0.527 g, 7.57 mmol) and the resulting solution was heated to 140° C. for 2 h. The reaction mixture was cooled in an ice bath and the solution partitioned between EtOAc and $H_2O$. The organic phase was separated, washed with brine, dried, filtered and concentrated in vacuo. The crude product was purified by $SiO_2$ chromatography eluting with 1% MeOH/DCM to afford 0.580 g of R-89b.

step 4—A suspension of R-89b (0.580 g, 1.06 mmol) and tosic acid (0.404 g, 2.13 mmol) in IPA (5 mL) was stirred at RT for 20 min. The solution was stirred at 80° C. until the reaction was complete. The reaction mixture was cooled in an ice-bath then $H_2O$ (10.6 mL), 20% aqueous $Na_2CO_3$ (2 mL) and $H_2O$ (5.3 mL) were added sequentially and the resulting mixture stirred at RT for 1 h. The resulting precipitate was collected, washed with $H_2O$ and dried in vacuo to afford 89 mg of R-90.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I

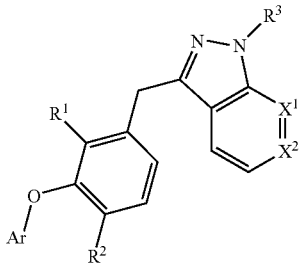

wherein:
$X^1$ and $X^2$ are N;
$R^1$ is fluorine or hydrogen;
$R^2$ is hydrogen, halogen, $C_{1-6}$ alkyl, $C_{3-7}$ cycloalkyl, $C_{1-6}$ haloalkyl, $C_{1-6}$ alkoxy, or $C_{1-6}$ alkylsulfonyl;
Ar is phenyl substituted with one to three groups independently selected in each occurrence from the group consisting of hydrogen, halogen, cyano, $C_{1-6}$ alkyl, $C_{1-6}$ alkoxy, $C_{1-6}$ haloalkyl and $C_{3-7}$ cycloalkyl;
$R^3$ is independently selected in each occurrence from the group consisting of:
(i) $CH_2OH$
(ii) $CH_2O—C(=O)(CH_2)_nCO_2R^4$ wherein n is 2 to 5;
(iii) $CH_2O—C(=O)CH_2OCH_2CO_2R^4$
(iv) $CH_2OCOR^5$;
(v) $CH_2OC(=O)CHR^6NH_2$;
(vi) $C(=O)R^5$; and,
(vii) $CH_2OP(=O)(OH)_2$;
$R^4$ is hydrogen or $C_{1-10}$ alkyl;
$R^5$ is hydrogen or $C_{1-10}$ alkyl, $C_{1-10}$ haloalkyl, $C_{1-10}$ aminoalkyl, $C_{1-3}$ alkylamino-$C_{1-10}$ alkyl, $C_{1-3}$ dialkylamino-$C_{1-10}$ alkyl, $C_{2-10}$ alkenyl, $C_{3-7}$ cycloalkyl, $C_{1-6}$ alkoxy,
$C_{1-10}$ aminoalkoxy, $C_{1-3}$ alkylamino-$C_{1-10}$ alkoxyl, $C_{1-3}$ dialkylamino-$C_{1-10}$ alkoxy, $NR^{7a}R^{7b}$, phenyl or pyridinyl said phenyl or pyridinyl ring optionally independently substituted with 1 to 3 substituents selected from the group consisting of halogen, $C_{1-10}$ alkyl, $C_{1-3}$ alkoxy, nitro and cyano;
$R^6$ is $C_{1-6}$ alkyl or the side chain of a naturally occurring amino acid;
$R^{7a}$ and $R^{7b}$ are independently hydrogen, $C_{1-6}$ alkyl or $C_{1-10}$ aminoalkyl, $C_{1-3}$ alkylamino-$C_{1-10}$ alkyl, $C_{1-3}$ dialkylamino-$C_{1-10}$ alkyl; or,
a pharmaceutically acceptable salt thereof.

2. A compound according to claim 1 wherein:
Ar is phenyl substituted with two groups independently selected in each occurrence from the group consisting of halogen, cyano and $C_{1-6}$ haloalkyl;
$R^1$ is fluoro;
$R^3$ is independently selected in each occurrence from the group consisting of:
(i) $CH_2O—C(=O)(CH_2)_nCO_2R^4$ wherein n is 2 to 5;
(ii) $CH_2OCOR^5$; and,
(iii) $C(=O)R^5$.

3. A compound according to claim 2 wherein $R^3$ is $CH_2O—C(=O)(CH_2)_2CO_2R^4$.

4. A compound according to claim 2 wherein Ar is 3,5-dicyano-phenyl, 3-chloro-5-cyano-phenyl or 3-cyano-5-difluoromethyl-phenyl; $R^2$ bromo, chloro or $C_{1-6}$ alkyl; and $R^3$ is $CH_2O—C(=O)(CH_2)_nCO_2R^4$.

5. A compound according to claim 1 which compound is selected from the group consisting of:
Succinic acid mono-{3-[4-bromo-3-(3-chloro-5-cyano-phenoxy)-2-fluoro-benzyl]-pyrazolo[3,4-c]pyridazin-1-ylmethyl}ester;
Succinic acid mono-{3-[4-bromo-3-(3,5-dicyano-phenoxy)-2-fluoro-benzyl]-pyrazolo[3,4-c]pyridazin-1-ylmethyl}ester;
Succinic acid mono-{3-[4-chloro-3-(3-chloro-5-cyano-phenoxy)-2-fluoro-benzyl]-pyrazolo[3,4-c]pyridazin-1-ylmethyl}ester;
3-[4-Bromo-3-(3-chloro-5-cyano-phenoxy)-2-fluoro-benzyl]-pyrazolo[3,4-c]pyridazine-1-carboxylic acid methyl ester;
Pentanedioic acid mono-{3-[4-bromo-3-(3-chloro-5-cyano-phenoxy)-2-fluoro-benzyl]-pyrazolo[3,4-c]pyridazin-1-ylmethyl}ester;
Acetic acid 3-[4-bromo-3-(3-chloro-5-cyano-phenoxy)-2-fluoro-benzyl]-pyrazolo[3,4-c]pyridazin-1-ylmethyl ester;
(S)-2-Amino-3-methyl-butyric acid 3-[4-bromo-3-(3-chloro-5-cyano-phenoxy)-2-fluoro-benzyl]-pyrazolo[3,4-c]pyridazin-1-ylmethyl ester;
{3-[4-Bromo-3-(3-chloro-5-cyano-phenoxy)-2-fluoro-benzyl]-pyrazolo[3,4-c]pyridazin-1-ylmethoxycarbonylmethoxy}-acetic acid;
3-[4-Bromo-3-(3-chloro-5-cyano-phenoxy)-2-fluoro-benzyl]-pyrazolo[3,4-c]pyridazine-1-carboxylic acid ethyl ester;
3-[4-Bromo-3-(3-chloro-5-cyano-phenoxy)-2-fluoro-benzyl]-pyrazolo[3,4-c]pyridazine-1-carboxylic acid isopropyl ester;
Succinic acid mono-{3-[4-chloro-3-(3,5-dicyano-phenoxy)-2-fluoro-benzyl]-pyrazolo[3,4-c]pyridazin-1-ylmethyl}ester;
3-[4-Bromo-3-(3-chloro-5-cyano-phenoxy)-2-fluoro-benzyl]-pyrazolo[3,4-c]pyridazine-1-carboxylic acid 2-dimethylamino-1-methyl-ethyl ester;
Pentanedioic acid mono-{3-[4-chloro-3-(3-chloro-5-cyano-phenoxy)-2-fluoro-benzyl]-pyrazolo[3,4-c]pyridazin-1-ylmethyl}ester;
Hexanedioic acid mono-{3-[4-bromo-3-(3-chloro-5-cyano-phenoxy)-2-fluoro-benzyl]-pyrazolo[3,4-c]pyridazin-1-ylmethyl}ester;
3-[3-(1-Acetyl-1H-pyrazolo[3,4-c]pyridazin-3-ylmethyl)-6-bromo-2-fluoro-phenoxy]-5-chloro-benzonitrile;
3-{6-Bromo-2-fluoro-3-[1-(pyridine-3-carbonyl)-1H-pyrazolo[3,4-c]pyridazin-3-ylmethyl]-phenoxy}-5-chloro-benzonitrile
3-[6-Bromo-2-fluoro-3-(1-isobutyryl-1H-pyrazolo[3,4-c]pyridazin-3-ylmethyl)-phenoxy]-5-chloro-benzonitrile; and
Phosphoric acid mono-{3-[4-bromo-3-(3-chloro-5-cyano-phenoxy)-2-fluoro-benzyl]-pyrazolo[3,4-c]pyridazin-1-ylmethyl}ester.

6. A pharmaceutical composition comprising a therapeutically effective quantity of a compound according to claim 1 and at least one carrier, excipient or diluent.

* * * * *